United States Patent
Schwartz

(10) Patent No.: US 10,226,474 B2
(45) Date of Patent: Mar. 12, 2019

(54) METHODS AND COMPOSITIONS FOR TREATMENT OF NON-ALCOHOLIC STEATOHEPATITIS

(71) Applicant: Temple University—Of The Commonwealth System of Higher Education, Philadelphia, PA (US)

(72) Inventor: Arthur G. Schwartz, Perkasie, PA (US)

(73) Assignee: TEMPLE UNIVERSITY—OF THE COMMONWEALTH SYTEM OF HIGHER EDUCATION, Philadelphia, PA (US)

(*) Notice: Subject to any disclaimer, the term of this patent is extended or adjusted under 35 U.S.C. 154(b) by 0 days.

(21) Appl. No.: 15/866,404

(22) Filed: Jan. 9, 2018

(65) Prior Publication Data

US 2018/0193356 A1  Jul. 12, 2018

Related U.S. Application Data

(60) Provisional application No. 62/443,897, filed on Jan. 9, 2017.

(51) Int. Cl.
 *A61K 9/00* (2006.01)
 *A61K 9/06* (2006.01)
 (Continued)

(52) U.S. Cl.
 CPC ........ *A61K 31/5685* (2013.01); *A61K 9/0014* (2013.01); *A61K 9/06* (2013.01);
 (Continued)

(58) Field of Classification Search
 CPC .. A61K 31/5685; A61K 47/10; A61K 9/0014; A61K 9/06; A61K 9/10; A61P 1/16
 See application file for complete search history.

(56) References Cited

U.S. PATENT DOCUMENTS 4,978,532 A  12/1990  El-Rashidy
5,157,031 A  10/1992  Schwartz et al.
(Continued)

FOREIGN PATENT DOCUMENTS

WO  WO-2016/161154 A1  10/2016

OTHER PUBLICATIONS

Te Sligte et al. (European journal of Internal Medicine, 15 (2004) pp. 10-21).*
(Continued)

*Primary Examiner* — Savitha M Rao
(74) *Attorney, Agent, or Firm* — Law Offices of Nanda P.B.A. Kumar, LLC

(57) ABSTRACT

A method for the treatment of an individual suffering from non-alcoholic steatohepatitis is provided comprising administering to the individual in need of such treatment an effective amount of a compound according to Formula I:

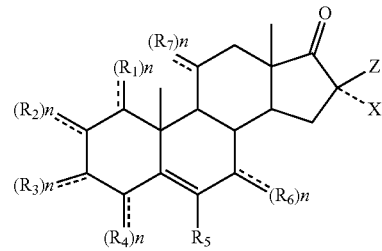

Formula I wherein:
$R_1$, $R_2$, $R_4$, $R_5$, $R_6$, and $R_7$ are each individually hydrogen, hydroxyl, —($C_1$-$C_6$)alkyl or —($C_1$-$C_6$)alkoxy;
each $R_3$ is individually halogen, hydrogen, hydroxyl, —($C_1$-$C_6$)alkyl or —($C_1$-$C_6$)alkoxy;
(Continued)

X is halogen, hydroxyl, hydrogen, —($C_1$-$C_6$)alkyl or —($C_1$-$C_6$)alkoxy;

Z is hydrogen, —($C_1$-$C_6$)alkyl or —($C_1$-$C_6$)alkoxy, and n is 1 or 2.

14 Claims, 18 Drawing Sheets

(51) Int. Cl.
| | |
|---|---|
| A61K 9/10 | (2006.01) |
| A61P 1/16 | (2006.01) |
| A61K 47/10 | (2017.01) |
| A61K 31/5685 | (2006.01) |

(52) U.S. Cl.
CPC .............. *A61K 9/10* (2013.01); *A61K 47/10* (2013.01); *A61P 1/16* (2018.01)

(56) References Cited

U.S. PATENT DOCUMENTS

| | | |
|---|---|---|
| 5,510,118 A | 4/1996 | Bosch et al. |
| 5,518,187 A | 5/1996 | Bruno et al. |
| 5,534,270 A | 7/1996 | De Castro |
| 5,543,133 A | 8/1996 | Swanson et al. |
| 5,656,621 A | 8/1997 | Schwartz et al. |
| 5,696,106 A | 12/1997 | Schwartz et al. |
| 5,700,793 A | 12/1997 | Schwartz et al. |
| 5,709,878 A | 1/1998 | Rosenbaum et al. |
| 5,744,462 A | 4/1998 | Schwartz et al. |
| 5,804,576 A | 9/1998 | Schwartz et al. |
| 5,858,410 A | 1/1999 | Muller et al. |
| 5,862,999 A | 1/1999 | Czekai et al. |
| 7,141,237 B2 | 11/2006 | Abram et al. |
| 8,431,555 B2 | 4/2013 | Schwartz et al. |
| 9,402,853 B2 | 8/2016 | Schwartz et al. |
| 9,408,856 B2 | 8/2016 | Schwartz et al. |
| 2003/0072807 A1 | 4/2003 | Wong et al. |
| 2004/0019026 A1 | 1/2004 | Schwartz |
| 2005/0234025 A1 | 10/2005 | Kutney et al. |
| 2007/0020197 A1 | 1/2007 | Galli et al. |
| 2007/0275068 A1 | 11/2007 | Martens et al. |
| 2012/0030779 A1 | 2/2012 | Benjamin et al. |
| 2013/0064815 A1 | 3/2013 | Coller |
| 2013/0196959 A1 | 8/2013 | Schwartz et al. |

OTHER PUBLICATIONS

Charlton et al. (Hepatology, vol. 47, issue 2, 2008, pp. 484-492).*
Offner et al. (Clinical immunology, 110 (2004) 181-190.*

International Search Report dated May 2, 2018 in International Patent Application PCT/US2018/013024, dated Jan. 9, 2018.
Ascaso, et al. "Diagnosing insulin resistance by simple quantitative methods in subjects with normal glucose metabolism," *Diabetes Care*, 26: 3320-3325 (2003).
Asgharpour et al., "A diet-induced animal model of non-alcoholic fatty liver disease and hepatocellular cancer," *J Hepatol.* 65(3):579-88 (2016). Epub May 31, 2016.
Harrison, "NASH, from diagnosis to treatment: where do we stand?" *Hepatology*, 62: 1652-1655 (2015).
Kernan, et al. "Pioglitazone after ischemic stroke or transietn ischemic attack," *NEJM*, 374:1321-1331 (2016).
Kim et al., "Association between non-invasive fibrosis markers and mortality among adults with nonaldoholic fatty liver disease in the United States," *Hepatology*, 57:1357-1365 (2013).
Kleiner et al, "Design and Validation of a Histological Scoring System for Nonalcoholic Fatty Liver Disease," *Hepatology*, 41(6):1313-1321 (2005).
Lattouf et al., "A useful tool to appraise collagen networks in normal and pathological tissues," *Official Journal of the Histochemical Society*, 62:751-758 (2014).
"Intercept Presents New Data Analyses on Non-Invasive Liver Testing From FLINT Trial of Obeticholic Acid in Nonalcoholic Steatohepatitis at AASLD 2015" Globe Newswire, New York, NY, Nov. 14, 2015 [online] [retrieved Jun. 3, 2018] Retrieved from the Internet: <URL:files.shareholder.com/downloads/AMDA-1AUOV7/0x0x861612/DD83A546-305C-4D45-9C5C-A04A5397775D/ICPT_News_2015_11_14_General_Releases.pdf>.
Lee et al., "Radiologic evalution of nonalcoholic fatty liver disease," World J Gastronenterol. 20(23):7392-7402 (2014).
Patel et al., "Nano suspension: a novel approach for drug delivery system," *Journal of Pharmaceutical Science and Bioscientific Research (JPSBR)*, 1(1):1-10 (2011).
Sanyal et al., "Piglitazone, Vitamin E, or placebo for nonalchoholic steatohepatitis," *NEJM*, 362: 1675-1685 (2010).
Sanyal et al., "Endpoints and clinical trial design for nonalcoholic steatohepatitis," *Hepatology*, 54:344-353 (2011).
Sanyal et al., "End points must be clinically meaningful for drug development in nonalcoholic fatty liver disease," *Gastroenterology*, 150: 11-13 (2016).
Schwartz et al., "Dehydroepiandrosterone, glucose-6-phosphate dehydrogenase, and longevity," Ageing Research Reviews 3(2):171-187 (2004) Abstract only.

* cited by examiner

METHODS AND COMPOSITIONS FOR TREATMENT OF NON-ALCOHOLIC STEATOHEPATITIS

CROSS-REFERENCE TO RELATED APPLICATION

This application claims the benefit of U.S. Provisional Application No. 62/443,897 filed Jan. 9, 2017 and the text of application 62/443,897 is incorporated by reference herein in its entirety.

FIELD OF THE INVENTION

The invention relates to methods and compositions for the treatment of non-alcoholic steatohepatitis (NASH).

BACKGROUND OF THE INVENTION

Hepatic steatosis or "fatty liver" is the accumulation of fat in the liver. Non-alcoholic fatty liver disease (NAFLD) requires that there is evidence of hepatic steatosis, either by histology or imaging, and there are no causes for secondary fat accumulation, such as significant alcohol consumption, use of steatogenic drugs, or hereditary disorder. NAFLD can be diagnosed by liver biopsy, ultrasonography, or, more recently, by magnetic resonance spectroscopy (MRS) or magnetic resonance imaging. (MRI). MRS and MRI are now regarded as the most accurate practical methods of measuring liver fat in clinical practice. Patients with NAFLD, i.e., simple steatosis or fatty liver, are thought to have benign prognoses with no evidence of increased mortality (Kim et al., *Hepatology*, 2013, 57:1357-1365; Sanyal et al., *Gastroenterology*, 2016, 150: 11-13).

Separate from NAFLD, non-alcoholic steatohepatitis (NASH) is a non-benign disorder characterized by substantial health risks. In addition to having excess fat in the liver, NASH is characterized by histologic evidence of hepatic inflammation and hepatocyte injury (ballooning), with or without fibrosis. NASH is characterized by increased risk of cardiovascular and liver-related mortality. NASH can lead to cirrhosis, in which the liver is permanently damaged and scarred. Cirrhosis results in fluid retention, muscle wasting, bleeding from the intestines, and liver failure. Liver transplantation is the only treatment for advanced cirrhosis with liver failure. Transplantation is increasingly performed in people with NASH. NASH is currently the number two reason for liver transplants, and it will very likely be number one by the end of the decade as new antiviral drugs control hepatitis C, which is presently the number one cause of liver failure.

NASH is typically diagnosed by liver biopsy and is based on histological evidence of steatosis, inflammation, and hepatocyte ballooning in the absence of other causes of liver disease or substantial alcohol consumption. The NAFLD Activity Score (NAS) was developed to provide a numerical score for patients who most likely have NASH. NAS is the sum of separate scores for steatosis (0-3), hepatocellular ballooning (0-2), and lobular inflammation (0-3), with a maximal score of 8. A score of ≥5 suggests probable NASH, and <3 indicates that NASH is unlikely. See, Kleiner et al, "Design and Validation of a Histological Scoring System for Nonalcoholic Fatty Liver Disease, Hepatology", 41(6): 1313-1321 (2005).

Although liver biopsy remains the gold standard for characterizing liver histology and diagnosing NASH, it is expensive and carries some morbidity and very rare mortality. Consequently, there is much interest in the development of non-invasive surrogate markers for the diagnosis of NASH, as well as the use of these markers to monitor the efficacy of experimental drugs in NASH clinical trials.

Currently, there is no USFDA-approved drug for the treatment of NASH. In 2009 the American Association for the Study of Liver Disease (AASLD) held a workshop on clinical trial design and end points for assessing treatment of NASH. Two histologic end points were proposed: 1) Resolution of steatohepatitis without worsening of fibrosis, and 2) at least a two-point improvement in NAS without worsening of fibrosis (Sanyal, A J, et al., *Hepatology*, 2011, 54:344-353).

There have been several randomized clinical trials using histology as the primary end point. In the Pioglitazone, Vitamin E, or Placebo for Nonalcoholic Steatohepatitis (PIVENS) trial, histologic response was determined by improvement in the ballooning score by ≥1 point; no increase in fibrosis; either a decrease in the NAS score to ≤3 or a decrease in the score of at least 2 points, with a 1 point decrease in lobular inflammation or steatosis score (Sanyal et al., *NEJM*, 2010, 362: 1675-1685). Vitamin E treatment produced a significant histologic improvement compared with placebo according to the above criteria, whereas the improvement with pioglitazone compared to placebo was not significant (p=0.04, with 0.025 considered statistically significant). However, both drugs are associated with significant side effects: an increased risk of prostate cancer with vitamin E and weight gain and increased risk of heart failure and fractures with pioglitazone.

The two experimental agents most advanced in clinical trials for the treatment of NASH are GFT 505, a dual PPAR α/δ agonist, and obeticholic acid (OCA), a farnesoid X nuclear receptor ligand. In a one-year phase 2 trial in NASH patients, an oral dose of 150 mg GFT 505 failed to produce a statistically significant improvement in histologically-assessed NASH vs. placebo. However, the drug did show a statistically significant improvement vs. placebo when patients with the mildest form of NASH (NAS<3) were excluded from analysis.

In a phase 2 trial (FLINT), obeticholic acid (25 mg) or placebo was administered to NASH patients for 72 weeks, with the primary outcome of a centrally scored liver histology, defined as a decrease in the NAS score of at least 2 points without worsening of fibrosis. Forty-five percent of obeticholic acid-treated patients achieved the primary end point vs. 23% of the placebo (p=0.002). However, despite these improvements in individual histological features, the proportion of patients with resolution of NASH, as determined from a baseline diagnosis to a non-NASH diagnosis, did not differ in patients treated with drug vs. placebo. The overall degree of histological improvement was similar to that seen with vitamin E and pioglitazone in the PIVENS Trial, although the two studies had somewhat different inclusion and exclusion criteria and primary end points.

Obeticholic acid treatment also produced a significant increase in plasma LDL and total cholesterol, as well as a decrease in insulin sensitivity, all of which could presage an increase in cardiovascular risk. Excess mortality in subjects with NASH is related to liver-related deaths, cardiovascular disease, and non-hepatocellular cancers. An ideal treatment for NASH should be one that improves not only liver disease, but also reduces the risks of cardiovascular outcomes and development of diabetes and cancers (Sanyal et al., *Hepatology*, 2011, 54: 344-353). Obviously, a drug that favorably impacts these various non-liver related indications, in addition to improving the liver disease per se, would be an attractive treatment for NASH.

SUMMARY OF THE INVENTION

A method for the treatment of an individual suffering from non-alcoholic steatohepatitis is provided comprising administering to the individual in need of such treatment an effective amount of a compound according to Formula I:

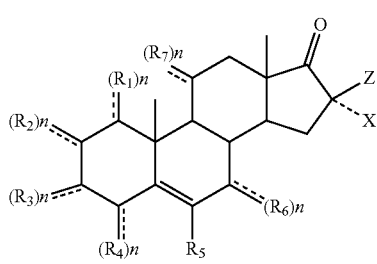

Formula I wherein:
$R_1$, $R_2$, $R_4$, $R_5$, $R_6$, and $R_7$ are each individually hydrogen, hydroxyl, —$(C_1$-$C_6)$alkyl or —$(C_1$-$C_6)$alkoxy;
each $R_3$ is individually halogen, hydrogen, hydroxyl, —$(C_1$-$C_6)$alkyl or —$(C_1$-$C_6)$alkoxy;
X is halogen, hydroxyl, hydrogen, —$(C_1$-$C_6)$alkyl or —$(C_1$-$C_6)$alkoxy;
Z is hydrogen, —$(C_1$-$C_6)$alkyl or —$(C_1$-$C_6)$alkoxy, and n is 1 or 2.

In certain embodiments, $R_1$, $R_2$, $R_4$, $R_5$, $R_6$, and $R_7$ are hydrogen.

In certain embodiments, the occurrences of halogen are independently selected from fluorine and chlorine.

In certain embodiments, the occurrences of —$(C_1$-$C_6)$alkyl are independently selected from —$(C_1$-$C_3)$alkyl, preferably ethyl and methyl.

In certain embodiments, the occurrences of —$(C_1$-$C_6)$alkoxy are independently selected from —$(C_1$-$C_3)$alkoxy, preferably ethoxy and methoxy.

In certain embodiments, each $R_3$ is individually hydrogen, halogen, hydroxyl or —$(C_1$-$C_6)$alkyl; X is hydrogen, halogen, hydroxyl or —$(C_1$-$C_6)$alkyl; and Z is hydrogen or —$(C_1$-$C_6)$alkyl.

In certain embodiments, each $R_3$ is individually hydrogen, halogen or —$(C_1$-$C_6)$alkyl; X is hydrogen, halogen or —$(C_1$-$C_6)$alkyl; and Z is hydrogen or —$(C_1$-$C_6)$alkyl.

In certain embodiments, at least one of X and Z is not hydrogen.

In certain embodiments, the compound of Formula I is selected from the group consisting of 5-androsten-17-one, 3β-fluoro-5-androsten-17-one, 3β-chloro-5-androsten-17-one, β3-methyl-5-androsten-17-one, 16α-hydroxy-5-androsten-17-one, 3β-methyl-16α-fluoro-5-androsten-17-one, 16α-methyl-5-androsten-17-one, 3β-methyl-16α-methyl-5-androsten-17-one, 3β-methyl-16α-chloro-5-androsten-17-one and 16α-fluoro-5α-androsten-17-one. Preferably, the compound is 16α-fluoro-5-androsten-17-one, also known as fluasterone.

A method for the treatment an individual suffering from non-alcoholic steatohepatitis comprising administering to the individual in need of such treatment a pharmaceutical composition comprising an effective amount of a compound according to Formula I:

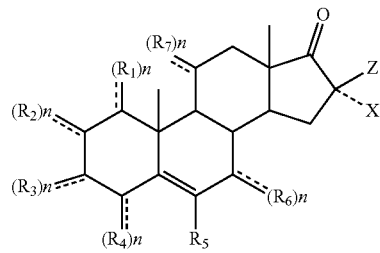

Formula I wherein:
$R_1$, $R_2$, $R_4$, $R_5$, $R_6$, and $R_7$ are each individually hydrogen, hydroxyl, —$(C_1$-$C_6)$alkyl or —$(C_1$-$C_6)$alkoxy;
each $R_3$ is individually halogen, hydrogen, hydroxyl, —$(C_1$-$C_6)$alkyl or —$(C_1$-$C_6)$alkoxy;
X is halogen, hydroxyl, hydrogen, —$(C_1$-$C_6)$alkyl or —$(C_1$-$C_6)$alkoxy;
Z is hydrogen, —$(C_1$-$C_6)$alkyl or —$(C_1$-$C_6)$alkoxy, and n is 1 or 2.

In certain embodiments, the compound of Formula I in the pharmaceutical composition is selected from the group consisting of 3β-methyl-16α-fluoro-5-androsten-17-one, 16α-methyl-5-androsten-17-one, 3β-methyl-16α-methyl-5-androsten-17-one, 3β-methyl-16α-chloro-5-androsten-17-one and 16α-fluoro-5-androsten-17-one. Preferably, the compound of Formula I is 16α-fluoro-5-androsten-17-one.

In certain embodiments, the pharmaceutical composition further comprises a surfactant. Preferably, the surfactant is polyoxyethylene-20-sorbitan monooleate (Tween 80).

In certain embodiments, the pharmaceutical composition is administered at a dose of from about 5 mg to about 150 mg per day. In certain embodiments, the pharmaceutical composition is administered subcutaneously or transdermally.

A method of reducing liver inflammation in an individual suffering from non-alcoholic steatohepatitis (NASH) comprises administering to the individual in need thereof an effective amount of a compound according to Formula I, as defined above. Preferably, the compound is in a pharmaceutical composition and is administered subcutaneously or transdermally.

A method of reducing hepatic fibrosis in an individual suffering from non-alcoholic steatohepatitis (NASH) comprises administering to the individual in need thereof an effective amount of a compound according to Formula I, as defined above. Preferably, the compound is in a pharmaceutical composition and is administered subcutaneously or transdermally In certain embodiments of the aforesaid therapeutic methods, the administration of a compound according to Formula I is carried out after identifying the subject as having NASH. Preferably, the compound is in a pharmaceutical composition and is administered subcutaneously or transdermally.

In certain embodiments of the aforesaid therapeutic methods, the subject is also suffering from one or more of hyperglycemia, diabetes (particularly type 2 diabetes), insulin resistance or impaired glucose tolerance.

In certain embodiments of the aforesaid therapeutic methods, a compound of Formula I is administered in the form of a pharmaceutical composition comprising nanosized particles of a compound of Formula I suspended in a mixture comprising a ($C_1$-$C_6$) alkyl alcohol, a surfactant, and optionally, a long chain alcohol.

In certain embodiments of the pharmaceutical composition comprising nanosized particles, the ($C_1$-$C_6$)alkyl alcohol is a ($C_1$-$C_3$)alkyl alcohol, preferably ethanol.

In certain embodiments, the surfactant is a polysorbate or a polyethyleneglycol substituted fatty acid. In certain embodiments, the polysorbate is selected from the group consisting of polyoxyethylene-20-sorbitan monooleate (Tween 80), polyoxyethylene-20-sorbitan monostearate (Tween 60), polyoxyethylene-20-sorbitan monopalmitate (Tween 40), polyoxyethylene-20-sorbitan monolaurate (Tween 20), polyethyleneglycol stearate, polyethyleneglycol oleate, and mixtures thereof. In certain embodiments of the pharmaceutical composition comprising nanosized particles, the polysorbate is polyoxyethylene-20-sorbitan monooleate (Tween 80), and wherein said pharmaceutical composition comprises a ($C_1$-$C_6$)alkyl alcohol in the range of from about 30 to about 90% (v/v), polyoxyethylene-20-sorbitan monooleate (Tween 80) in the range of from about 0.01% to about 3.5% and water in the range of from about 0% to about 60%.

In certain embodiments of the pharmaceutical composition comprising nanosized particles, the long chain alcohol corresponds to the formula $CH_3(CH_2)_n$—OH, wherein n is an integer in the range of 9-24. In certain embodiments, the long chain alcohol is selected from the group consisting of decyl alcohol, cetyl alcohol, stearyl alcohol, lauryl alcohol, myristyl alcohol, oleyl alcohol and mixtures thereof.

In certain embodiments of the pharmaceutical composition comprising nanosized particles, the composition further comprises water.

In certain embodiments, the pharmaceutical composition comprising nanosized particles comprises a transdermal delivery system.

In certain embodiments, the pharmaceutical composition comprising nanosized particles is in the form of a gel comprising a ($C_1$-$C_6$) alkyl alcohol, preferably ethanol; a surfactant; water; a thickening agent; and optionally a base. In certain embodiments, the gel comprises from about 30 to about 90% (v/v) ($C_1$-$C_6$) alkyl alcohol, preferably ethanol; and from about 0.01 to about 5% (v/v) surfactant. In certain embodiments, the base is present and is selected from the group consisting of triethanolamine, diethanolamine and triethylamine.

Also provided is a compound of Formula I, for treatment of non-alcoholic steatohepatitis.

Also provided is a compound of Formula I, for preparation of a medicament for treatment of non-alcoholic steatohepatitis.

Also provided is a use of a compound of Formula I, for preparation of a medicament for treatment of non-alcoholic steatohepatitis.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the principles of the invention.

DEFINITIONS

Figure 1:
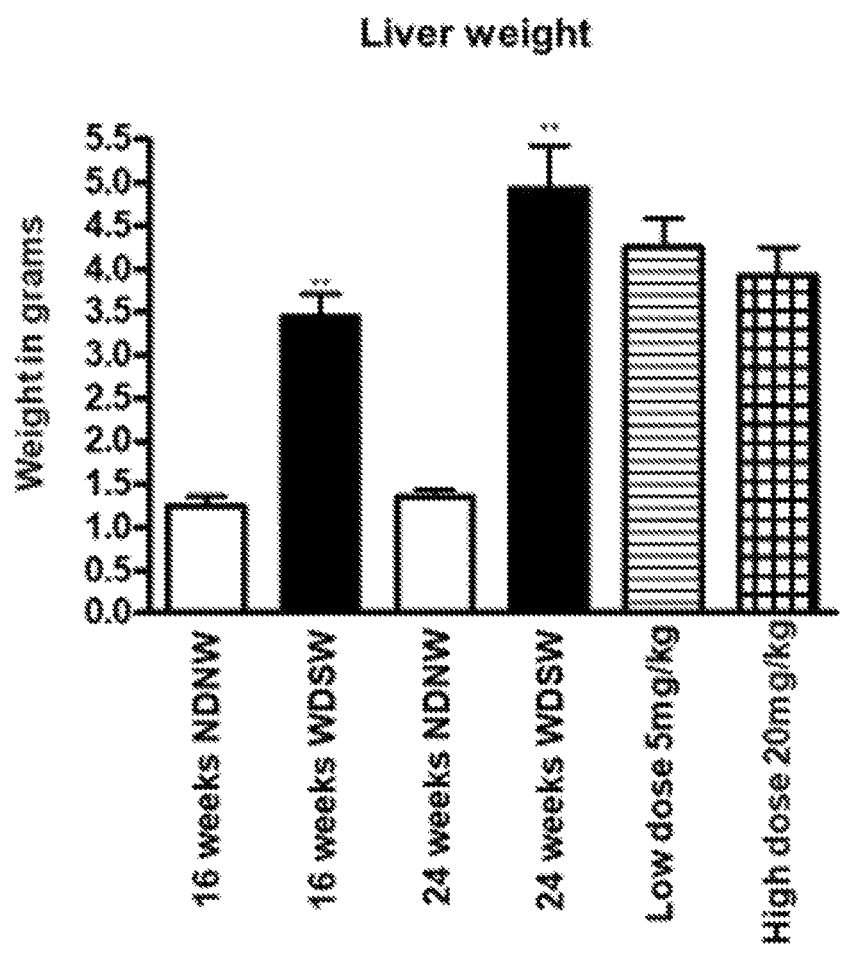
FIG. 1 is a diagram showing a histogram analysis of liver weight of mice 16 weeks on Normal Diet Normal Water (NDNW/NCNW; negative control) vs 16 weeks Week on Western Diet Sugar Water (WDSW; Positive Control) (P value P<0.001); and 24 weeks on NDNW vs 24 weeks on WDSW (P value P<0.001). [Are the low dose and high data for 24 weeks on WDSW?]

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. Thus, recitation of "a cell", for example, includes a plurality of the cells of the same type.

"About" as used herein when referring to a measurable value such as an amount, a temporal duration, and the like, is meant to encompass variations of +/−20% or +/−10%, more preferably +/−5%, even more preferably +/−1%, and still more preferably +/−0.1% from the specified value, as such variations are appropriate to perform the disclosed methods.

The term "alkyl", by itself or as part of another substituent means, unless otherwise stated, a straight or branched chain hydrocarbyl having the designated number of carbon atoms (i.e., $C_1$-$C_6$ means one to six carbons). Examples include: methyl, ethyl, propyl, isopropyl, butyl, isobutyl, tert-butyl, pentyl, neopentyl, and hexyl. Most preferred is ($C_1$-$C_3$)alkyl, particularly methyl and ethyl.

The term "alkoxy" employed alone or in combination with other terms means, unless otherwise stated, an alkyl group, as defined above, connected to the rest of the molecule via an oxygen atom, such as, for example, methoxy, ethoxy, 1-propoxy, 2-propoxy (isopropoxy) and the higher homologs and isomers. The alkyl portion of the alkoxy group can have a designated number of carbon atoms as defined for alkyl groups above. Preferred are ($C_1$-$C_3$)alkoxy, particularly methoxy and ethoxy.

An "effective amount" as used herein, means an amount of compound, when administered to a patient suffering from NASH, provides a therapeutic benefit in alleviating one or more manifestations of the NASH. It is understood, however, that the full therapeutic effect does not necessarily occur by administration of one dose, and may occur only after administration of a series of doses. Thus, an effective amount may be administered in one or more administrations.

The terms "halo" or "halogen" by themselves or as part of another substituent mean, unless otherwise stated, a fluorine, chlorine, bromine, or iodine atom. Preferably, a halogen includes fluorine, chlorine, or bromine, more preferably, fluorine or chlorine.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds. The individual is, in one embodiment, a human being.

"Non-alcoholic steatohepatitis" or "NASH" means steatohepatitis characterized by at least one of lobular inflammation and hepatocyte ballooning in the absence of other causes of liver disease or substantial alcohol consumption. NASH is characterized by a NAFLD Activity Score (NAS) of 5 or more, where NAS is the sum of separate scores for steatosis (range: 0-3), hepatocellular ballooning (range: 0-2), and lobular inflammation (range: 0-3). See Kleiner et al., supra. The steatosis score represents the percent of hepatocytes containing fat droplets (steatosis) as 0 (<5%), 1 (5-33%), 2 (33-66%), and 3 (>66%). Hepatocyte ballooning is scored as 0 (none), 1 (few), or 2 (many cells with prominent ballooning). Lobular inflammation is scored according to the number of foci of inflammation: 0 (no foci), 1 (<2 foci/200× field), and 2 (2-4 foci/200× field).

As used herein, the term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

As used herein, the terms "treat" and "treatment" in connection with NASH are used interchangeably and are meant to indicate the taking of steps to obtain beneficial or desired clinical results in an individual suffering from NASH, including the postponement of further disease progression, or reduction in the severity of symptoms that have or are expected to develop, ameliorating existing symptoms and preventing additional symptoms. An end point for NASH treatment may comprise an improvement in NAS score by at least one unit, more preferably at least two units, without worsening of fibrosis. Alternatively, and end point for NASH treatment may comprise resolution of steatohepatitis, without worsening of fibrosis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within

9 that range, for example, 1, 2, 2.7, 3, 4, 5, 5.3, and 6. This applies regardless of the breadth of the range.

DETAILED DESCRIPTION OF THE INVENTION

Individuals suffering from non-alcoholic may be treated by administration of a compound according to Formula I:

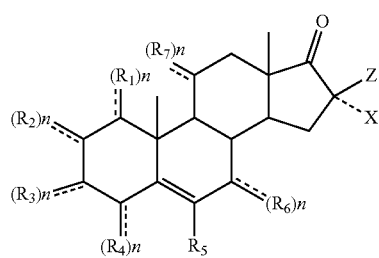

Formula I wherein:

$R_1$, $R_2$, $R_4$, $R_5$, $R_6$, and $R_7$ are each individually hydrogen, hydroxyl, —$(C_1$-$C_6)$alkyl or —$(C_1$-$C_6)$alkoxy;

each $R_3$ is individually halogen, hydrogen, hydroxyl, —$(C_1$-$C_6)$alkyl or —$(C_1$-$C_6)$alkoxy;

X is halogen, hydroxyl, hydrogen, —$(C_1$-$C_6)$alkyl or —$(C_1$-$C_6)$alkoxy;

Z is hydrogen, —$(C_1$-$C_6)$alkyl or —$(C_1$-$C_6)$alkoxy, and n is 1 or 2.

The compounds of Formula I include stereoisomers, such as optical isomers, diastereomers and geometrical isomers, or tautomers depending on the mode of substitution. The compounds may contain one or more chiral centers and occur as racemates, racemic mixtures and as individual diastereomers, enantiomeric mixtures or single enantiomers, or tautomers, with all isomeric forms being included in the present invention. The present invention is meant to comprehend all such isomeric forms of the compounds in the compositions of the present invention, and their mixtures. Therefore, where a compound is chiral, the separate enantiomers, substantially free of the other, are included within the scope of the invention; further included are all mixtures of the two enantiomers.

The stereochemistry of various substituents are designated as being in the α-position by means of a broken line (---) joining the substituent to the steroid nucleus. The substituents are designated as being in the β-position by means of a solid line (-) joining the substituent to the steroid nucleus. In those cases in which the substituents may be either in the α or β positions, the substituents are indicated as being joined to the steroid nucleus by a broken line and a solid line placed side-to-side.

The compounds of Formula I can be prepared by art-recognized techniques. Exemplary procedures are described in U.S. Pat. Nos. 5,700,793 and 5,804,576, the entire contents of which are incorporated by reference herein.

Preferred compounds include those in which $R_1$, $R_2$, $R_4$, $R_5$, $R_6$, and $R_7$ are hydrogen.

Further preferred are compounds wherein each $R_3$ is individually hydrogen, halogen, hydroxyl or —$(C_1$-$C_6)$ alkyl; X is hydrogen, halogen, hydroxyl or —$(C_1$-$C_6)$alkyl; and Z is hydrogen or —$(C_1$-$C_6)$alkyl.

Further preferred are compounds wherein each $R_3$ is individually hydrogen, halogen or —$(C_1$-$C_6)$alkyl; X is hydrogen, halogen or —$(C_1$-$C_6)$alkyl; and Z is hydrogen or —$(C_1$-$C_6)$alkyl.

10

Further preferred are compounds wherein at least one of X and Z is not hydrogen.

Preferred compounds include 5-androsten-17-one, 3β-fluoro-5-androsten-17-one, 3β-chloro-5-androsten-17-one, 3β-methyl-5-androsten-17-one, 16α-hydroxy-5-androsten-17-one, 3β-methyl-16α-fluoro-5-androsten-17-one, 16α-methyl-5-androsten-17-one, 3β-methyl-16α-methyl-5-androsten-17-one, 3β-methyl-16α-chloro-5-androsten-17-one and 16α-fluoro-5α-androsten-17-one. Most preferred is 16α-fluoro-5α-androsten-17-one, also known as fluasterone.

Selection of Patients for Treatment

Patients treated according to the present disclosure are afflicted with NASH. The presence of NASH may be established by a liver biopsy revealing a NAS score prior to treatment of 5 or more. A NAS score is generated upon biopsy according the criteria set forth in Kleinen et al., supra.

Steatosis is the abnormal retention of lipids within the liver. Patients treated for NASH according to the present invention can have a NAS steatosis score of 1, 2 or 3. Lobular inflammation is also evaluated upon liver biopsy and scored with values of 0-3. Patients to be treated for NASH can have lobular inflammation scores of 0, 1, 2 or 3, and a ballooning score of 0, 1 or 2, provided that the sum of the lobular inflammation score and the ballooning score is at least 2.

NASH patients may or may not display fibrosis. Fibrosis is not a component of the NAS score. The separation of fibrosis from other functions of activity is an accepted paradigm for staging and grading NASH may also be evaluated upon liver biopsy. Fibrosis is scored with values of 0-4, the scores being defined as: 0 represents no fibrosis, 1 represents perisinusoidal or periportal fibrosis, 1a represents mild, zone 3, perisinusoidal fibrosis; 1b represents moderate zone 3, perisinusoidal fibrosis; 1c represents portal/periportal fibrosis; 2 represents perisinusoidal and portal/periportal fibrosis; 3 represents bridging fibrosis; and 4 represents cirrhosis. (See Kleiner et al., supra. Patients treated according to the present invention can have a fibrosis stage score of 0-3. After treatment, patients can have a fibrosis stage score that is at least no worse than the baseline score before treatment, and alternatively can have a reduction in the fibrosis stage score of at least one level, alternatively at least two or three levels.

While selection of patients based on a NAS score is based on liver biopsy, not excluded from the scope of the present invention is the utilization of surrogate markers which parallel the histological evaluation of a NAS score (Kleiner et al., supra).

Therapeutic Administration

The compounds of Formula I may be administered in a convenient manner. Suitable topical routes include oral, rectal, inhaled (including nasal), topical (including buccal and sublingual), transdermal and vaginal, preferably across the epidermis. The compound of Formula I can also be used for parenteral administration (including subcutaneous, intravenous, intramuscular, intradermal, intraarterial, intrathecal and epidural), and the like, but this route is not preferred owing to the nature of the active ingredient. It will be appreciated that the preferred route may vary with for example the condition of the recipient. An advantage of the compositions of this invention is that they can be administered transdermally, which is the preferred route of administration.

The physician will determine the dosage of the active agent which will be most suitable and it will vary with the form of administration and the particular compound chosen, and furthermore, it will vary depending upon various factors, including but not limited to the patient under treatment and the age of the patient, the severity of the condition being treated and the like. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. When given parenterally, the compounds are administered to generally in dosages of, for example, about 0.1 to about 10 mg/kg/day, also depending upon the host and the severity of the condition being treated and the compound utilized. The dosage is preferably administered once daily, although dividing this recommended daily dose to provide multiple administrations is possible.

When give transdermally to humans, a dose of the active agent may range, for example, from about 12 mg to about 150 mg, more preferably from about 24 mg to about 100 mg. The dosage is preferably administered once daily, although dividing this recommended daily dose to provide multiple administrations is possible.

Compounds of Formula I require high oral doses in mammals to produce efficacy, in view of first pass metabolism. A dose of at least 200 mg/kg of oral fluasterone has been shown to be effective in other indications, e.g., abolishing TPA-stimulated epidermal hyperplasia in mouse skin, whereas when administered by subcutaneous injection the lowest effective dose was 2.5 mg/kg. See U.S. Pat. No. 8,431,555, the entire disclosure of which is incorporated herein by reference. A human oral dose of compound of Formula I is therefore believed to be at least about 1200 mg.

In particular embodiments, the compounds utilized are orally administered in amounts ranging from about 15 mg to about 45 mg per kilogram of body weight per day, depending upon the particular mammalian host and more preferably from about 20 to about 40 mg/kg body weight per day, most preferably from about 25 to about 35 mg/kg body weight per day.

Dosage regimens may be adjusted by the physician to provide the optimum therapeutic response. For example, several divided doses may be administered daily or the dose may be proportionally reduced as indicated by the exigencies of the therapeutic situation. Higher or lower doses than recited herein are also contemplated, as it may be necessary to use dosages outside these ranges in some cases.

A daily dosage may be divided, such as being divided equally into two to four times per day daily dosing. Compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The treatment may be carried out for as long a period as necessary, either in a single, uninterrupted session, or in discrete sessions. The treating physician will know how to increase, decrease, or interrupt treatment based on patient response. The treatment schedule may be repeated as required. According to one embodiment, compound of Formula I is administered once daily. As NASH is a chronic disease, the period of therapy could be indefinite.

Treatment efficacy is generally determined by improvement in histological end points, as determined by liver biopsy. Two histologic end points have been proposed by the American Association for the Study of Liver Diseases (AASLD) for treatment of NASH: (1) resolution of steatohepatitis without worsening of fibrosis, and (2) at least a two-point improvement in NAS without worsening of fibrosis (Sanyal, et al., *Hepatology*, 2011, 54:344-353). Resolution of NASH may also be defined as: total absence of hepatocellular ballooning (score=0) and absent or mild inflammation (score 0-1), with steatosis present or absent (score 0-3). It may be understood that these various criteria may change, depending on guidance from regulatory agencies.

In addition to these aforementioned histological end points, fibrosis regression may also be a suitable surrogate marker for drug benefit, since worsening of fibrosis would indicate a more likely progression to cirrhosis. Fibrosis staging can only be performed by liver biopsy, although non-invasive markers for fibrosis are under development (Harrison, *Hepatology*, 2015, 62: 1652-1655).

In addition to end-points based on liver histology, serum markers of liver fibrosis may be monitored to assess treatment efficacy. Two serum markers of liver fibrosis, FIB-4 and APRI, have recently been shown to be associated with mortality in individuals diagnosed with NAFLD. In a recent epidemiological study, in a group of 11,154 participants, 34% were diagnosed by ultrasound to have NAFLD (fatty liver). Over a median follow-up of 14.5 years, within the NAFLD cohort there was a progressive increase in mortality, after adjustment for other known predictors of mortality, with advancing fibrosis scores, as determined by FIB-4 or APRI (Kim et al., *Hepatology* 2013, 57: 1357). The increased mortality was almost entirely from cardiovascular causes. Importantly, the NAFLD cohort, when compared to the cohort without NAFLD, did not show an increase in mortality. Mortality was significantly increased only in the NAFLD subpopulation with advanced fibrosis.

In the phase 2 (FLINT) trial, treatment with OCA for 72 weeks significantly reversed liver fibrosis (determined by biopsy) in NASH patients. OCA treatment also led to a significant reduction in both the FIB-4 and APRI scores compared to baseline. Importantly, investigators found that a decline in the FIB-4 score of 10% after 24 weeks predicted improvement in fibrosis by at least one stage as determined by biopsy at 72 weeks. Likewise, a 34% reduction in APRI score predicted improvement in fibrosis by at least one stage at 72 weeks ("Intercept Presents New Data Analyses on Non-Invasive Liver Testing From FLINT Trial of Obeticholic Acid in Nonalcoholic Steatohepatitis at AASLD 2015" GLOBE NEWSWIRE, New York, N.Y., Nov. 14, 2015). Accordingly, non-invasive measures of fibrosis to monitor treatment efficacy may be employed, avoiding the need for repeated liver biopsy.

APRI and FIB-4 scores are calculated by the following published formulas (Kim, et al., *Hepatology* 2013, 57: 1357), wherein "PLT count" is the platelet count; "AST" is aspartate transaminase, and the upper limit of normal is 40 IU/ml; and "ALT" is alanine aminotransferase:

$$APRI = ([AST/\text{upper limit of normal}]/PLT\ count[10^9/L])$$

$$FIB\text{-}4 = (age\ [years] \times AST\ [IU/L])/(PLT\ [10^9/L] \times (ALT\ [IU/L])^{1/2}).$$

The method of treating NASH with a compound of Formula I may have additional health benefit in patients also suffering from type 2 diabetes or either impaired glucose tolerance or impaired fasting glucose (pre-diabetic). See U.S. Pat. No. 8,431,555. Fluasterone in particular is effective in reducing hyperglycemia in a mouse diabetic model. Lowering plasma glucose levels in NASH patients would be anticipated to produce health benefits independent of improvement of their liver disease.

In addition to treating hyperglycemia, compounds of Formula I find utility in treatment of insulin resistance, a condition resulting from impaired insulin signaling. See U.S. Pat. No. 8,431,555. Thus, the method of treating NASH with a compound of Formula I may have additional health benefit in patients also suffering from insulin resistance.

Insulin resistance is essentially universal in type 2 diabetics, but is also very common in non-diabetics, particularly in the overweight and obese population. In a recent study, treating non-diabetic, insulin-resistant individuals, who suffered a recent ischemic stroke or transient ischemic attack, with the insulin sensitizer, pioglitazone, significantly reduced their risk of subsequent stroke or heart attack (Kernan, et al. NEJM, 2016, 374: 1321). Insulin resistance was defined as value of ≥3.0 on the homeostasis model assessment of insulin resistance (HOMA-IR) index. The HOMA-IR value is calculated as level of fasting glucose (millimoles/liter) times the level of fasting insulin (microunits/milliliter) divided by 22.5. The value of 3.0 was chosen since this level identifies the highest quartile among populations without diabetes (Ascaso, et al. Diabetes Care, 2003, 26: 3320).

The thiazolidinedione (TZD) drugs, pioglitazone and rosiglitazone, which are approved for treating hyperglycemia in type 2 diabetes, increase insulin sensitivity, but have numerous side effects (weight gain, fluid retention, increased incidence of heart failure, fractures), which have greatly curtailed their use. Compounds of Formula I such as fluasterone, have a different mechanism of action from the TZD's, lacks their side effects and can be used as a safer drug to improve insulin sensitivity.

Formulation

The compounds of Formula I may be combined with a pharmaceutically acceptable carrier, for administration in the form of a pharmaceutical composition. The active ingredient or agent in such formulations (i.e. a compound of Formula I) may comprise from 0.1 to 99.99 weight percent of the formulation. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., Remington's Pharmaceutical Sciences, 18th Edition (1990), Mack Publishing Co., Easton, Pa. Suitable dosage forms may comprise, for example, tablets, capsules, solutions, parenteral solutions, troches, suppositories, creams, ointments, gels and transdermal devices (patches).

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl or propyl paraben, and chlorbutanol. The composition for parenteral administration may take the form of an aqueous or nonaqueous solution, dispersion, suspension or emulsion. Where the parenteral administration is transdermal, the composition advantageously takes the form of a gel or patch.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

Compounds of Formula I having low water solubility may benefit from formulation with certain mixtures of surfactants and/or organic alcohols that significantly improve solubility. Modalities for formulation of low solubility compounds of Formula I are described in U.S. Pat. No. 8,431,555, the entire disclosure of which is incorporated herein by reference. Such improved solubility is useful for preparing pharmaceutical formulations containing compounds of Formula I for topical, transdermal, oral and subcutaneous administration. Preferable surfactants include polysorbates, and long-chain organic alcohols, including fore example cetyl alcohol, stearyl alcohol. Polysorbate is used as the preferred surfactant, with Polysorbate 80 (polyoxyethylene (20) sorbitan monooleate; Tween 80) being an especially preferred surfactant. Sorbitan monooleate or other polysorbates with varying polyoxyethylene chain lengths can also be used. Straight chain organic alcohols with chain lengths in the range of 8-30 carbons are also useful as surfactants. Especially preferred carbon chain length is in the range of 14-24. Such compounds can correspond to the formula $CH_3(CH_2)_nOH$, wherein n is 13-23. Another group of compounds useful as surfactants is polyethyleneglycol conjugated fatty acids and alcohols. Particularly preferred in this group of surfactants are the polyethyleneglycol stearate (MYRJ™ 45), Macrogol stearyl ether 2 (BRIJ™72), Macrogol stearyl ether 20 (BRIJ™72P), Macrogol stearyl ether 20-23 (BRIJ™35P), Macrogol stearate 40-50 (MYRJ™52S), Macrogol stearate 100 (MYRJ™25P), Macrogolglycerol hydroxystearate 25 (ATLAS™), Macrogolglycerol lauryl ether 9 and Macrogolglycerol lauryl ether 9. Sorbitan substituted fatty acids are also useful as surfactants in formulations of Formula I. For example, sorbitan laureate, sorbitan stearate, sorbitan oleate and sorbitan trioleate can be used.

In one embodiment, the formulation can be in the form of aqueous gel, an anhydrous gel, a water-in-oil emulsion, oil-in-water emulsion or a suspension. Examples of gel forming procedures for DHEA can be found in U.S. Pat. Nos. 5,709,878, and 4,978,532 the entire contents of which are incorporated by reference herein. Such gel formation techniques may be utilized to formulate compounds of Formula I. Gels are semisolid systems of either containing suspended small inorganic particles (two phase gels) or organic macromolecules interpenetrated by a liquid (single phase gels). Emollients such as petrolatum, paraffin wax, beeswax, cetyl palmitate, and lanolin can be included in the formulations herein. When formulated for presentation as a gel, the composition of the invention can include a gelling agent such as a finely divided solid and/or a thickener in concentrations that produce a loose molecular network inhibiting the free movement of liquid ingredients. Thus a typical gel composition of the invention includes a concentration of a compound of Formula I in the range of about 0.1 to about 20 grams per 100 grams of composition, preferably about 0.25 to about 5 grams per 100 grams; a concentration of phospholipid in the range of about 2 to about 50 grams per 100 grams of composition, preferably about 3 to about 25 grams per 100 milliliters; a concentration of finely divided solid in the range of about 0 to about 15 grams per 100 grams of composition, and a concentration of thickener in the range of about 0 to about 15 grams per 100 grams of composition.

Gellants may also be included in the formulations. These agents are typically nonionic or cationic polymers such as hydroxyethyl cellulose, methylcellulose, guar gum, xanthan gum, hydroxypropylcellulose and cationic cellulosics. A particular example is Sepigel.

In one embodiment, a gel comprising a compound of Formula I, can be made by mixing a $(C_1-C_6)$alkyl alcohol, a surfactant (e.g., a polysorbate or a polyethylene glycol-substituted fatty acid), water and a compound of Formula I and, optionally, adding and mixing a thickening agent followed by incubating the ingredients until gel formation. Various temperatures may be used for incubation to effect gel formation. A preferred temperature range is about 3° C. to about 90° C.; a more preferred range is about 10° C. to about 50° C.; and more preferred range is about 10° C. to about 40° C. Incubation times vary depending on the temperature, and the ratio of ingredients. The ratios of ingredients may also vary depending on the particular compound of Formula I and the particular $(C_1-C_6)$alkyl alcohol use. The composition may comprise alcohol in the range of from about 20 to about 95% (v/v); preferably from about 30 to about 90%; even more preferably about 50 to about 90%. The water content may from about 0 to about 60%; preferably about 2 to about 40%; more preferably about 5 to about 30%; even more preferably about 15 to about 30%. The surfactant may be present in the range of about 0 to 10%; more preferably about 0.01% to about 5%; even more preferably about 0.01% to about 3.5%.

Examples of thickening agents that can be added to the gel or solution formulations described herein include: cellulosic thickening agents, for example, cellulose, hydroxyethylcellulose, carboxymethylcellulose, and hydroxypropylmethyl cellulose; and acrylic thickening agents. Examples of preferred acrylic thickeners are carbomers, for example, non-linear polymers of acrylic acid cross-linked with a polyalkenyl polyether. Examples of preferred carbomers which may be used in the present invention include carboxypolymethylene, carboxyvinyl polymer, and alkyl acrylates, for example, acrylic acid/alkyl methacrylate copolymer. All of the above are available from Noveon, with carboxypolymethylene sold as Carbopol 980®, carboxyvinyl polymer sold as Carbopol 940®, and acrylic acid/alkyl methacrylate copolymer sold as Pemulen TR-1®.

In an embodiment, the formulation can be applied by misting or spraying the formulation on the skin either via a metered dose device or from a unit dose container. In this method, the formulation can be distributed evenly over a larger area thereby providing a quick means for absorption. Alternatively, the formulation can be applied via an applicator, such as a roll-on applicator, a metered pump dispenser or sponge.

In one embodiment, a compound of Formula I is administered to the recipient by means of a transdermal delivery system or patch. Transdermal delivery is accomplished by exposing a source of the substance to be administered to the recipient's skin for an extended period of time. Typically, the formulation is incorporated in or absorbed on a matrix or container from which it is released onto the recipient's skin. The rate of release can be controlled by a membrane placed between the container and the skin, by diffusion directly from the container, or by the skin itself serving as a rate-controlling barrier. Many such suitable transdermal delivery systems and containers are known, ranging in complexity from a simple gauze pad impregnated with the substance to be administered and secured to the skin with an adhesive bandage to multilayer and multi-component structures. Some of the systems are characterized by the use with the substance to be administered of a shaped article sufficiently flexible to snugly fit to the skin of the recipient and thus serve both as container from which the substance is delivered to the recipient's skin and as barrier to prevent loss or leakage of the substance away from the area of the skin to which the substance is to be delivered. A transdermal delivery system or patch may also contain an added substance that assists the penetration of the active ingredient through the skin, usually termed a skin enhancer or penetration enhancer. Transdermal delivery systems may contain an ethoxylated oil such as ethoxylated castor oil, ethoxylated jojoba oil, ethoxylated corn oil, and ethoxylated emu oil. An alcohol mixed with the ethoxylated oil may form a penetration enhancer.

In a preferred method for the treatment of an individual suffering from non-alcoholic steatohepatitis, a pharmaceutical composition containing an effective amount of a compound according to Formula I is administered. The compound can be any of 3β-methyl-16α-fluoro-5-androsten-17-one, 16α-methyl-5-androsten-17-one, 3β-methyl-16α-methyl-5-androsten-17-one, 3β-methyl-16α-chloro-5-androsten-17-one or 16α-fluoro-5-androsten-17-one, or a combination of these compounds. The composition can include a surfactant (e.g., a polysorbate or a polyethyleneglycol substituted fatty acid). Such a pharmaceutical composition is administered to an individual in need of the treatment (e.g., human patient) at a dose of from about 5 mg to about 150 mg of the Formula I compound per day (for example about 5 mg, about 10 mg, about 15 mg, about 20 mg, 25 mg and 30 mg and so on). The pharmaceutical composition can administered by, for example, subcutaneous injection or transdermal delivery. See also Example 5 herein. The compound of the Formula I (e.g., fluasterone) may be in the form of nanosized particles suspended in a mixture comprising a $(C_1-C_6)$ alkyl alcohol, a surfactant, and optionally, a long chain alcohol.

A topical oil-in-water emulsion composition can be prepared by making a solution of compound of Formula I and adding an immiscible phase (e.g., a biocompatible oil phase) and an optional emulsifying agent. An irritation mitigating agent can also be included, such as $(C_{12-15})$ alkyl benzoate, octyl methoxycinnamate, octyl dimethyl PABA, octocrylene, menthyl anthranilate, and homomenthyl salicylate.

In certain embodiments a foam comprising a compound of Formula I can be prepared. An example of a foam forming procedure can be found in U.S. Pat. No. 7,141,237. For instance, an active agent in a solution as described herein and a quick-breaking foaming agent comprising a mixture of cetyl alcohol and stearyl alcohol, which are dissolved in the ethanol solution can be used. The composition may be packaged in a polyamide-imide-lined aluminum can and pressurized with a propane/butane mixture as the propellant.

Under the packaged pressure, the hydrocarbon propellant liquefies and becomes miscible with the water/ethanol solution.

The pharmaceutical compositions for delivery of active agent may contain an emulsifier and/or surfactant. A wide variety of such agents can be employed. In one embodiment, the compositions of the present invention comprise from about 0.05% to about 95%, preferably from about 10% to about 80%, and more preferably from about 3.5% to about 60% of at least one surfactant. The surfactant, at a minimum, must be hydrophilic enough to disperse in ethanol or other solvent system. The surfactants useful herein can include any of a wide variety of cationic, anionic, zwitterionic, and amphoteric surfactants. The exact surfactant chosen will depend upon the pH of the composition and the other components present.

In one embodiment, the composition comprises a hydrophilic emulsifier or surfactant. The compositions preferably comprises from about 0.05% to about 5%, more preferably from about 0.05% to about 3.5% of at least one hydrophilic surfactant. Without intending to be limited by theory, it is believed that the hydrophilic surfactant assists in dispersing hydrophobic materials.

Preferred hydrophilic surfactants are selected from nonionic surfactants. Among the nonionic surfactants that are useful herein are those that can be broadly defined as condensation products of long chain alcohols, e.g. $C_{8-30}$ alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside and lauryl polyglucoside.

Other useful nonionic surfactants include the condensation products of alkylene oxides with fatty acids (i.e. alkylene oxide esters of fatty acids); the condensation products of alkylene oxides with 2 moles of fatty acids (i.e. alkylene oxide diesters of fatty acids); the condensation products of alkylene oxides with fatty alcohols (i.e. alkylene oxide ethers of fatty alcohols); and the condensation products of alkylene oxides with both fatty acids and fatty alcohols. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Other nonionic surfactants suitable for use herein include sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of $C_1$-$C_{30}$ fatty alcohols, polyglyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, and mixtures thereof. Nonlimiting examples of these non-silicon-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, PEG-100 stearate, and mixtures thereof. Commercially available surfactants include polysorbate 80 (Tween 80), polysorbate 20 (Tween 20), polysorbate 40 (Tween 40) and polysorbate (60). The preferred surfactants include polysorbates and more preferred surfactant is Tween 80.

Other emulsifiers useful herein are fatty acid ester blends based on a mixture of sorbitan or sorbitol fatty acid ester and sucrose fatty acid ester, the fatty acid in each instance being preferably $C_8$-$C_{24}$, more preferably $C_{10}$-$C_{20}$. The preferred fatty acid ester emulsifier is a blend of sorbitan or sorbitol $C_{16}$-$C_{20}$ fatty acid ester with sucrose $C_{10}$-$C_{16}$ fatty acid ester, especially sorbitan stearate and sucrose cocoate.

The hydrophilic surfactants useful herein can alternatively or additionally include any of a wide variety of cationic, anionic, zwitterionic, and amphoteric surfactants known in the art. The cationic surfactants useful herein include cationic ammonium salts such as quaternary ammonium salts, and amino-amides.

A wide variety of anionic surfactants are also useful herein. Nonlimiting examples of anionic surfactants include the alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., alkali metal salts, e.g., sodium or potassium salts) of fatty acids.

Amphoteric and zwitterionic surfactants are also useful. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., $C_{12}$-$C_{30}$), and alkanoyl sarcosinates.

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 1% to about 90%, more preferably from about 1% to about 60% of one or more structuring agents.

Suitable structuring agents are selected from the group consisting of palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, and mixtures thereof.

The compounds of Formula I may also be formulated according to U.S. Patent Publication No. 2004/0019026, describing pharmaceutical use of 5-androsten-17-one derivatives. The entire disclosure of Publication No. 2004/0019026 is incorporated herein by reference.

Another aspect of the invention herein is the use of micronized or nanosized particles composed of a compound of Formula I, in particular, fluasterone. Such compositions comprise colloidal dispersions of such particles in a liquid, which may be stabilized by surfactants. In particularly, production of drugs as nanosuspension are useful as an oral formulation, or for non-oral administration. Micronized or nanosized formulations of fluasterone are described in, for example, in U.S. Pat. No. 8,431,555. In nanosuspensions, the drug is maintained in the required crystalline state with reduced particle size, leading to an increased dissolution rate and therefore improved bioavailability. See, Patel et al., *Journal of Pharmaceutical Science and Bioscientific Research (JPSBR)*, 1(1):1-10, 2011. Because of the high adhesiveness of nanoparticles on biological surfaces (e.g., epithelial gut wall), nanoparticulate technology may also prolong the absorption time of poorly soluble drugs, thereby improving bioavailability.

There are several well-known methods for the preparation of nanosized pharmaceuticals. For example, wet milling or piston gap homogenization can be used to nanosize fluasterone. For discussions related to wet milling, see, e.g., U.S. Pat. No. 5,518,187; U.S. Pat. No. 5,862,999; and U.S. Pat. No. 5,534,270; for discussions related to piston gap homogenization, see U.S. Pat. No. 5,543,133; U.S. Pat. No. 5,858,410; U.S. Patent Publication No. 2003/0072807 A1; and U.S. Pat. No. 5,510,118, the complete disclosures of which are herein incorporated by reference. Wet milling is a well understood process, which relies on impact and shear forces to reduce particle size. Piston gap homogenization, which utilizes cavitation forces and impact or shear forces to reduce particle size. A method involving high-pressure spray homogenizer can also be used to prepare nanosized particles. (U.S. Patent Publication No. 20070020197). Wet grinding may be accomplished in, for example, a DeltaVita® grinding system (NETZSCH Premier Technologies, LLC, Exton, Pa.).

The nanosized particles employed in the composition have a median particle size of about 1 nm to less than 1000 nm, preferably about 50 nm to about 600 nm, more preferably about 100 nm to about 500 nm, and even more preferably about 100 nm to about 400 nm, most preferably about 100 nm to about 300 nm.

As used herein, "micronized" refers to objects having an average size ranging from 1 micron to 1000 micron, as measured by light-scattering methods, microscopy, or other appropriate methods. The micronized compositions preferably have particle size in the range of about 1 micron to 1000 micron, more preferably about 1 micron to 100 micron, even more preferably about 1 micron to 50 micron, even more preferably about 1 micron to 25 micron, most preferably about 1 micron to 10 micron.

The nanosized or micronized compounds of Formula I can be part of a delivery matrix. For example, a matrix carrier can be an amorphous microporous non-fibrous silicon or titanium oxide similar to those described in U.S. Patent Publication No. 20070275068. Sol-gel processed drug-silica composite materials have been investigated for controlled drug release. One concept involving the use of sol-gel type silica is the synthesis of a bio-erodible silica-drug composite. Silica-based drug release systems prepared using sol-gel approaches in which compounds of Formula I are introduced during polymerization and processing of the silica matrix can be used for drug delivery. An alternative approach for making a drug delivery system based on silica gels is the synthesis of silica in the absence of compounds of Formula I, followed by drying and calcination to obtain a xerogel and then by loading the calcinated material with the appropriate compound. The sol-gel approach enables the synthesis of a large variety of silica materials. Micropores with very narrow pore size distribution can be obtained through calcinations which can be useful for the delivery of micronized or nanosized compounds of Formula I, particularly for topical delivery.

A preferred nanosuspension of a Formula I compound comprises $(C_1-C_6)$alkyl alcohol in the range of from about 30 to about 90% (v/v), surfactant (e.g., polyoxyethylene-20-sorbitan monooleate (Tween 80)) in the range of from about 0.01% to about 3.5%; and water in the range of from about 0% to about 60%.

EXAMPLES

The practice of the invention is illustrated by the following non-limiting examples.

Example 1—Fluasterone Nanosuspension

A nanosuspension of fluasterone is prepared as follows. Prior to preparation of the nanosuspension, a particle size analysis is carried out on the bulk fluasterone used in the preparation. The dry bulk fluasterone powder is dispersed in water. Particle size analysis is carried out in a Model 770 AccuSizer, a light obscuration device of high resolution with a lower size limit of +0.50 m. The median particle size on a number distribution basis and volume distribution basis is determined.

To form the nanosuspension, an aliquot of the bulk fluasterone powder is suspended at a concentration of 25 mg/mL in a vehicle of 48.8% ethanol, 48.8% water, and 2.5% Tween-80 and placed in an Avestin C-5 Homogenizer for 3 hours at 20,000 psi. The nanosuspension is analyzed on the same AccuSizer device for particle size determination. A target median particle size on a number distribution basis is 0.60 μm and on a volume distribution basis is 0.64 μm. Corresponding target mean particle sizes are 0.62 μm are 2.12 μm.

In order to determine stability of the nanosuspension, the nanosuspension is kept approximately one month at ambient temperature and reanalyzed for particle size distribution on the AccuSizer device.

Example 2—Fluasterone Treatment of NASH in CDAA Diet Model

C57BL/6 mice (or a similar strain) are utilized in the following study to determine the efficacy of fluasterone in treating NASH. C57BL/6 mice treated for 22 weeks with a choline-deficient L-amino acid defined diet (CDAA) develop the histologic features of NASH (steatosis, hepatocyte ballooning, and inflammation) as well as fibrosis (Miura et al. Gastroenterology, 2010, 139: 323-334), with a NAFLD activity score (NAS) of ~6.5. The mice also develop obesity, insulin resistance, and dyslipidemia (high plasma cholesterol and triglycerides), and recapitulate both the associated metabolic and liver histologic features of NASH.

Groups of mice are treated with varying doses of fluasterone (2.5 mg/kg, 5 mg/kg, 10 mg/kg, or 20 mg/kg) or control vehicle. Fluasterone is administered transdermally (to a shaved area on the back) in a nanosized fluasterone suspension (25-50 mg/ml) in 48.8% water, 48.8% ethanol, and 2.5% Tween 80. Fluasterone or control vehicle is administered once daily. In addition to transdermal administration, fluasterone is administered subcutaneously at the same dosages. Micronized fluasterone, suspended in a suitable vehicle such as 95% saline-5% Tween 80, is utilized for subcutaneous injection.

After ~22 weeks, mice are euthanized and liver tissue is prepared for determination of liver histopathology. Liver histology is assessed using hematoxylin and eosin staining, and fibrosis is determined by both Masson's trichrome and Sirius Red stains according to established methodology. See, Lattouf et al., *Official Journal of the Histochemical Society*_62:751-758 (2014).

Liver histology is evaluated by an expert pathologist blinded to control or drug treatment. The degree of steatosis, lobular inflammation, and hepatocellular ballooning is scored using NASH-Clinical Research Network criteria, as described in Asgharpour et al., J. Hepatol., 2016, 65: 579-588. Briefly, the percent of hepatocytes containing fat droplets (steatosis) is scored as 0 (<5%), 1 (5-33%), 2 (33-66%), and 3 (>66%). Hepatocyte ballooning is scored as 0 (none), 1 (few), or 2 (many cells with prominent ballooning). Foci of inflammation is scored as 0 (no foci), 1 (<2 foci/200× field), and 2 (2-4 foci/200× field). As described previously, the NAFLD activity score (NAS) is determined as the sum of the various scores, with a maximum of 8.

Fibrosis is scored by histological criteria, as described in Asgharpour et al., supra, as well as by quantitative analysis by morphometry from digitalized Sirius-Red stained sections.

Example 3—Fluasterone Treatment of NASH in Streptozocin/High Fat Diet Model

According to a further mouse model of NASH, NASH is induced by low dose streptozotocin (STZ) treatment followed by feeding high-fat diet (HFD). In this model, C57BL/6J male mice are treated with 200 μg STZ at 2 days after birth and are fed ad libilum HFD after 4 weeks of age (Fujii et al. Med. Mol. Morphol., 2013, 46: 141-152). By 12 weeks of age, treated mice develop histologic features of NASH (NAS ~5.2) as well as liver fibrosis. Mice are treated with fluasterone according to the treatment protocols of Example 2. Evaluation of liver histology is carried out according to Example 2, except that mice are euthanized at about 12 weeks of age.

Example 4—Fluasterone Treatment of NASH

A course of treatment of a NASH patient, may be as follows. A patient with histologically-diagnosed NASH (NAS≥4, fibrosis ≥2) is be treated once daily transdermally with fluasterone hydroalcoholic gel (containing 25-100 mg/ml nanosized fluasterone) at a dose of 25 to 100 mg. After about 72 weeks of treatment the patient will undergo liver biopsy. A positive treatment outcome is resolution of NASH without worsening of fibrosis. Resolution of NASH is defined as: total absence of hepatocellular ballooning (score=0) and absent or mild inflammation (score 0-1), with steatosis present or absent (score 0-3). It may be understood that these criteria may change, depending on guidance from regulatory agencies.

One or both of the serum markers of liver fibrosis, FIB-4 and APRI, are optionally analyzed to determine achievement of treatment efficacy. APRI and FIB-4 scores are calculated by the following published formulas from Kim et al., *Hepatology* 2013, 57: 1357), wherein PLT means platelet, AST is aspartate transaminase, "upper limit of normal" is 40 IU/ml and ALT is alanine aminotransferase:

APRI is=([AST/upper limit of normal]/PLT count $[10^9/L]$)

FIB-4=(age [years]×AST [IU/L])/(PLT $[10^9/L]$×(ALT $[IU/L])^{1/2}$).

Example 5—Efficacy of Fluasterone in the Treatment or Reversal of NASH Development and Progression in the DIAMOND™ Mouse Model DIAMOND™ (Diet Induced Animal Model of Non-alcoholic fatty liver Disease) mouse model is a mouse model of NASH. This mouse model was used to assess the effect of fluasterone. The drug formulation (subcutaneous injectable formulation) contained fluasterone as an active pharmaceutical ingredient in a vehicle. The vehicle contained RO (reverse osmosis) water mixed with sterile saline solution and 5% Tween-80. The drug formulation was prepared as follows: micronized powder of fluasterone (submicron range particles of fluasterone) was suspended in the vehicle and vortexed to evenly suspend. Two doses of fluasterone were used and compared to vehicle controls and positive and negative natural history controls to determine the impact on weight gain, fatty liver, steatohepatitis, and the progression to fibrosis. The two different doses of fluasterone used were (i) a low dose (LD) fluasterone (5 mg fluasterone/kg body weight) for 8 weeks and (ii) a high dose (HD) fluasterone (20 mg fluasterone/kg body weight) for 8 weeks. Vehicle Control was sterile saline with 5% Tween-80. The other details are as follows: (1) Animal Species: DIAMOND™ Mice (Male C57BL/6J(B6)-129s1/SvImJ(S129)). (2) Positive Control and Treatment Groups' food and drinking water: (a) Food—Western Diet ENVIGO Harlan/Teklad 42% Adjusted Calories from Fat (TD. 88137), and (b) RO Water—Sugar Water—D-fructose Alfa Aesar #A17718 and D-glucose Water—Fisher Scientific #D19-212; Recipe=231 g Fructose+189 g Glucose+750 ml RO (reverse osmosis) water Diluted into 9 L RO Water. This diet is referred to herein as Western Diet Sugar Water (WDSW). (3) Negative Control Group's food and drinking water: (a) Normal Mouse Chow Diet—ENVIGO Harlan/Teklad Normal Rodent Chow (TD 7012 Teklad LM-485), and (b) RO water. This diet is referred to herein interchangeably as Normal Diet Normal Water (NDNW) and Normal Chow Normal Water (NCNW).

Eight-two (82) DIAMOND™ mice were put on the special diet WDSW (high fat diet (Harlan/Teklad 42% fat) and sweetened water (D-Fructose and D-Glucose)) at time point 0 (t=0) (at eight weeks of age). Mice were weighed weekly. Of these, 10 mice were injected subcutaneously with fluasterone at concentration 5 mg/kg and 10 mice were injected subcutaneously with fluasterone at concentration 20 mg/kg, and 5 mice in a staggered group were injected with vehicle starting at 16 weeks on diet (t=16) until 24 weeks (t=24), as described in "Subcutaneous Injection." For baseline controls, 8 male DIAMOND™ mice were placed on the WDSW at eight weeks of age and given no treatment; these were the positive natural history controls. A second group of 8 male DIAMOND™ mice were continued on the NCNW/NDNW at eight (8) weeks and these were the negative natural history control group. The mice were weighed weekly. At 16, 20, and 24 weeks on diet, fasting insulin was measured in serum from tail vein nick. HOMA-IR scores were calculated. 8 mice on WDSW and 8 mice NDNW were sacrificed at 16 weeks (t=16) on diet as baseline positive and negative controls. 8 mice on WDSW and 8 mice NDNW were sacrificed at 24 weeks (t=24). Carbon dioxide was used as an anesthetic and a cardiac puncture was performed for exsanguination. Cervical dislocation was performed as a secondary means of euthanasia.

As discussed above, the drug formulation used in this experiment contained fluasterone as an active pharmaceutical ingredient in a vehicle. The vehicle contained RO water mixed with sterile saline solution and 5% Tween-80.

All protocols were approved by the Institutional Animal Care and Use Committee (IACUC). All measures were taken to ensure the welfare, safety, health and comfort of the animals and to minimize stress and pain. Procedures such as necropsy were performed using IACUC-approved protocols for euthanasia. The specific methodology followed was as follows:

Body Weights: Mice were weighed weekly and the weights determined the amount of test compound administered.

Subcutaneous Injection: The mice received a subcutaneous injection 1× daily. In summary, mice were grasped at the scruff of the neck and a suitable place was selected for the injection. The injection site was moved daily to ensure limited distress to the animal. A pattern, developed in conjunction with the institutional veterinarian, was established to rotate the injection sites to allow adequate healing of the sites. In order to reduce the chance of infection due to multiple injections in one location, a different quadrant (cranial, paramedial abdomen left, paramedial abdomen right, and caudal) was injected each day and the injection pattern was repeated every 4 days (e.g., day 1=cranial quadrant, day 2=paramedial abdomen left quadrant, day 3=paramedial abdomen right quadrant, and day 4=caudal quadrant then repeated following this same pattern throughout the experimental period). Additionally, careful monitoring was used to assure the needle went into the subcutaneous layer of the skin to form a bolus and sufficiently absorbed. The mice were monitored for up to 1-hour post-procedure for adverse signs. Abnormal signs could have included tearing marks, abnormal bleeding, swelling at the site of the injection, hunched posture, redness and increased temperature at the injection site, and a rough hair coat.

Euthanasia: Mice were administered carbon dioxide as prescribed by the American Veterinary Association (5% induction) and exsanguinated. Secondary euthanasia was performed by cervical dislocation. The carcasses were disposed of according to the approved institutional standards.

Blood collection: The mice were fasted for 6 hours prior to euthanasia. Blood collection took place during euthanasia via cardiac puncture. The blood was collected into serum separator tubes, spun at 5,000 RPM for 15 minutes at 4 degrees Celsius, aliquoted into Eppendorf tubes, and serum was then snap-frozen to −80° C. and stored in a −80° C. freezer until pulled and thawed for analysis. Lipid (total cholesterol, LDL, HDL, triglycerides, HDL calc.) and hepatic (ALB, ALP, AST, ALT, BUN, GGT and TBIL) panels were performed within one week of necropsy.

Blood Glucose Measurement: At necropsy, one drop of whole blood from the cardiac puncture was placed on a test strip and inserted into the OneTouchPlus Ultra Glucometer.

Serum Lipid Profile Measurement: 40-50 microliters of thawed serum was placed into the sample well of an AL-10-991 test cassette, then the test cassette was placed into the Alere Cholestech LDX blood lipid analyzer for readouts: total cholesterol (T-chol); triglycerides (trigs) (45 lower LOD); glucose (standard range); HDL (100 upper LOD); and LDL (calculated T-chol-HDL).

Serum LFT Measurement: Abaxis VS2 blood chemistry analyzers were used for measuring LFTs. Phenobarbital test rotors (catalog #500-0049) which measure AST, ALT, ALP, GGT, ALB, and T Bil were used. The reactions were colorimetric, read automatically by the VS2.

Insulin Measurement: Plasma insulin levels were measured using the Mercodia Mouse Insulin ELISA kit (cat#10-1247-01, lot#25427) following the manufacturer's protocol. Briefly, 10 µl of Calibrators or 10 µl of plasma were added to coated wells and incubated for 2 hours with shaking at room temperature (RT). Subsequently, wells were washed 6 times, and incubated for 15 min at RT with TMB reaction substrate before addition of stop solution. Results were read on a Molecular Devices SpectraMax M5 plate reader at 450 nm wavelength using SoftMax Pro 6.4 within 30 minutes of reaction stop. Samples were run in duplicate and insulin quantified by comparison to the standard curve.

HOMA-IR: The mice were fasted for six (6) hours prior to collection of blood from a tail nick. The blood was measured by glucometer and insulin ELISA. HOMA IR was calculated by the following Formula using the insulin measurements above and the fasting blood glucose measurements obtained at necropsy. HOMA IR=insulin (mU/L) *glucose (mmol/L)/22.5.

HOMA IR was calculated for WDSW, Low Dose and High Dose treatment groups, compared to each other and to their respective baselines (data not shown). HOMA IR, like insulin, was comparable between the positive WDSW control and the drug treated groups. The baseline insulin and HOMA IR did continue to worsen throughout the treatment process as indicated by the statistically significant difference between the baseline and final measurements in the drug treated groups. However, since fasting blood glucose was improved, one can still conclude that there was an improvement in insulin sensitivity even though the absolute insulin amounts were not significantly different.

As described above, mice were grouped into 5 groups: high dose (20 mg/kg), low dose (5 mg/kg), vehicle control (VC), WD/SW positive natural history control (PC) and NC/NW (or ND/NW or normal chow/normal water) negative natural history control (NC). The data presented in various Figures herein is to be understood by reference to these different groups.

Shown in FIG. 1 is liver weight data. 16 weeks NDNW vs 16 weeks WDSW (P value P<0.001). 24 weeks NDNW vs 24 weeks WDSW (P value P<0.001). The fluasterone-treated mice had smaller livers than the WDSW positive control group, however the difference was not statistically significant. The high dose had smaller livers compared to the WDSW 24 wk control group (P=0.054); the P value for the low dose group was P=0.12.

Figure 2:
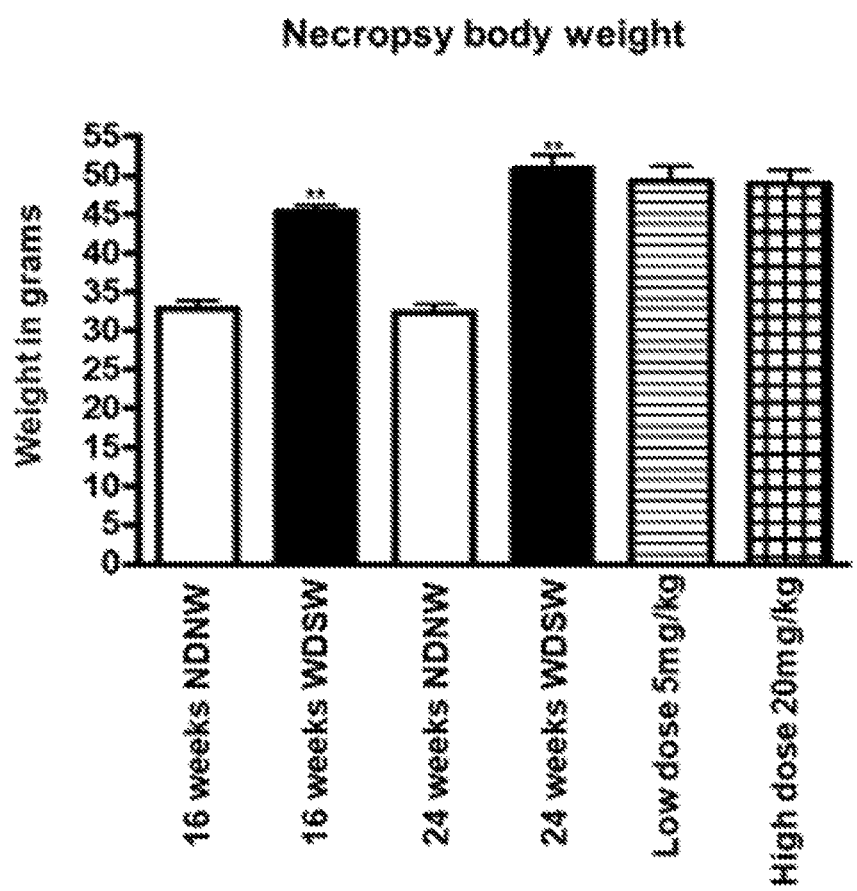
FIG. 2 is a diagram showing a histogram analysis of body weight of mice 16 weeks on NDNW vs 16 weeks on WDSW (P value P<0.001); and 24 weeks on NDNW vs 24 weeks on WDSW (P value<0.001).

Shown in FIG. 2 is necropsy body weight data. The fluasterone treated mice had body weights at necropsy comparable to the 24 week positive WDSW controls. Body weights were randomized prior to going on-diet and beginning dosing, and were comparable between groups.

Figure 3:
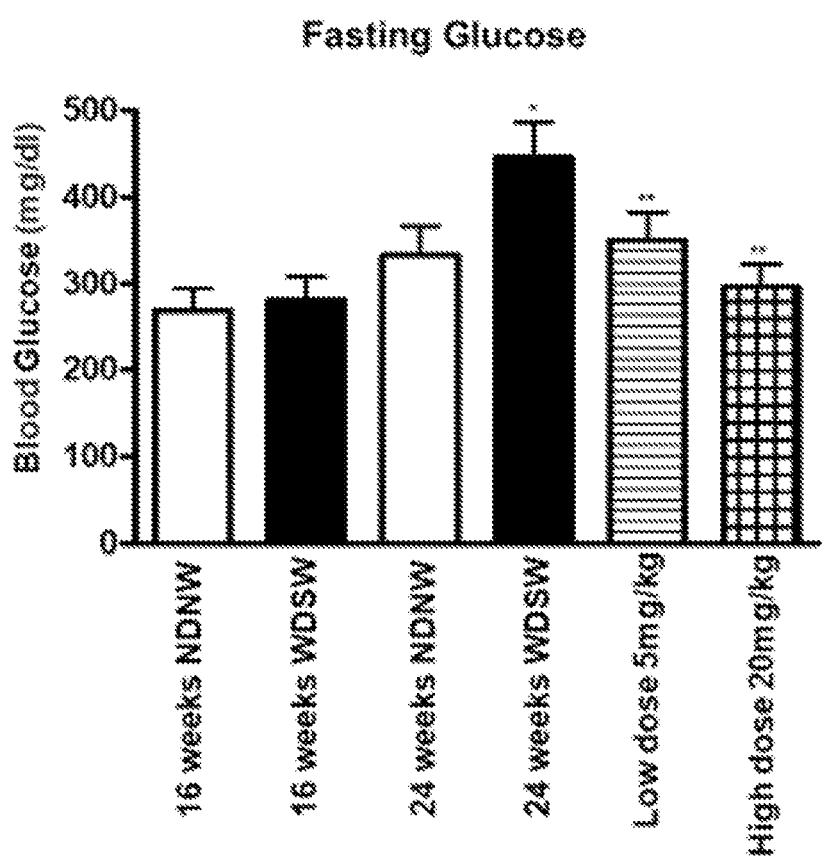
FIG. 3 is a diagram showing a histogram analysis of fasting blood glucose in mice 24 weeks NDNW vs 24 weeks WDSW (P value P<0.02); 24 weeks WDSW vs 24 weeks low dose 5 mg/Kg (P value P: 0.003); and 24 weeks WDSW vs 24 weeks high dose 20 mg/Kg (P value P: 0.003).

Shown in FIG. 3 is fasting blood glucose data. Fasting blood glucose was significantly improved in the fluasterone-treated mice, both low and high dose.

Figure 4:
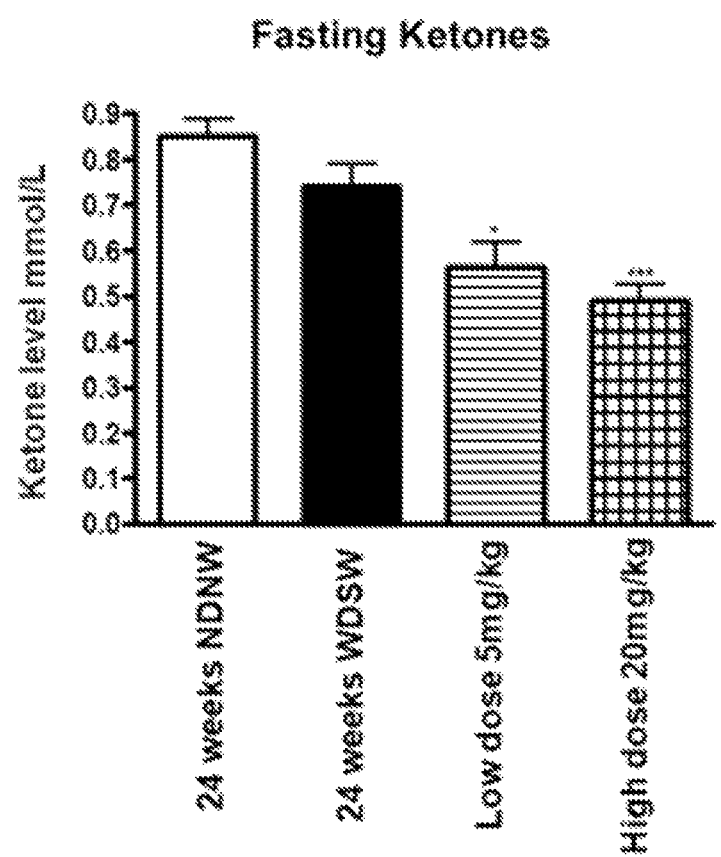
FIG. 4 is a diagram showing a histogram analysis of fasting ketones in mice 24 weeks on WDSW vs 24 weeks low dose 5 mg/Kg (P value P: 0.01); and 24 weeks on WDSW vs 24 weeks high dose 20 mg/Kg (P value P: 0.0005).

Shown in FIG. 4 is fasting blood ketones data. Fasting blood ketones were significantly lower in both fluasterone-treated groups at necropsy.

Figure 5A:
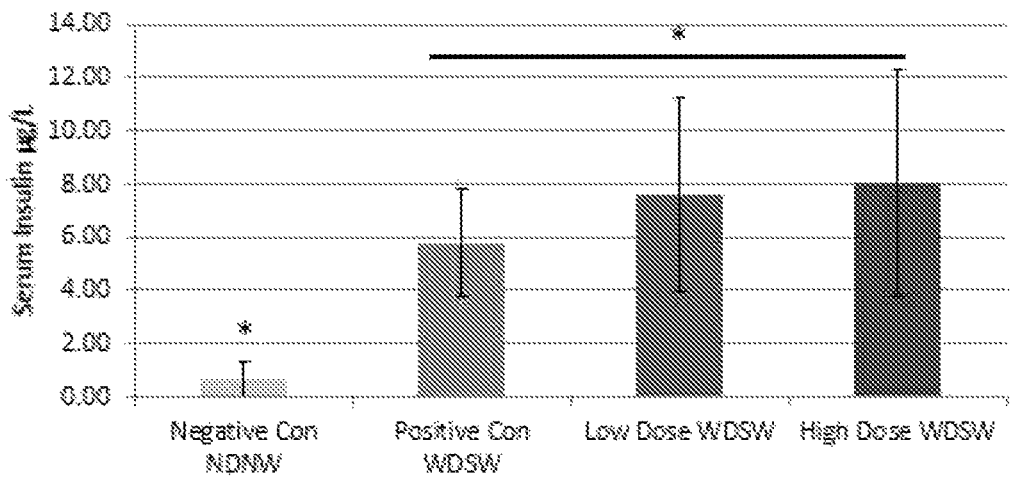
FIGS. 5A and 5B are diagrams showing histogram analyses of 16 week insulin measurements (5A) and 24 week insulin measurements (5B).
Figure 5B:
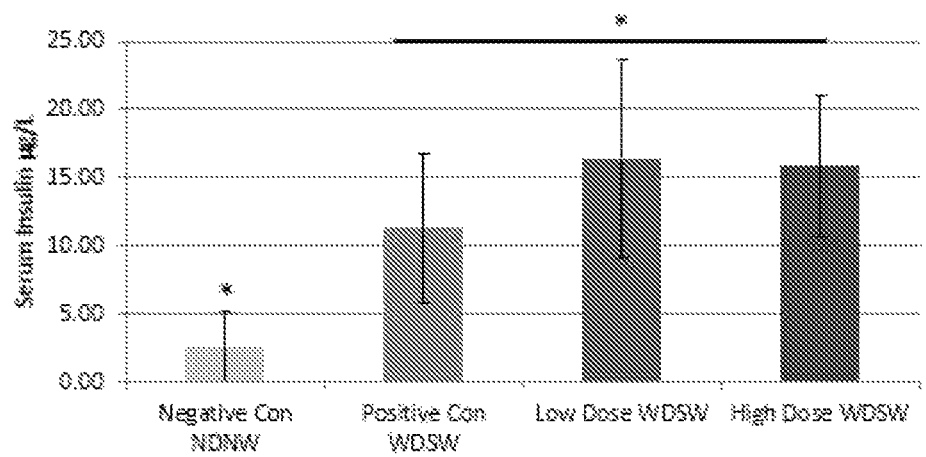

Shown in FIGS. 5A and 5B are fasting insulin data. At the beginning of dosing (baseline, 16 weeks) and end of study (24 weeks, after 8 weeks of dosing), fasting insulin was measured by ELISA. At both baseline and end of study, the fasting insulin measurements were not statistically significant between drug treated groups and WDSW positive control. All 3 WDSW groups had significantly higher insulin levels than the negative control, at both baseline and end of study.

Figure 6:
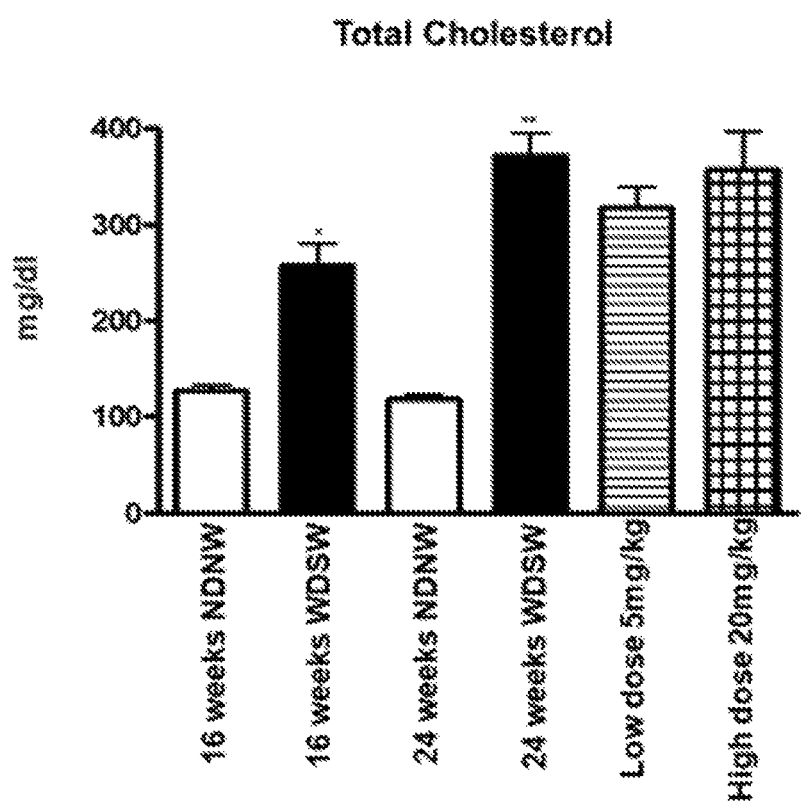
FIG. 6 is a diagram showing a histogram analysis of total serum cholesterol in mice 16 weeks NDNW vs 16 weeks WDSW (P value P<0.05); and 24 weeks NDNW vs 24 weeks WDSW (P value P<0.001).

Shown in FIG. 6 is total cholesterol data. There was lower total serum cholesterol in the fluasterone-treated mice relative to the WDSW positive controls; in the low dose group, the P=0.0504.

Figure 7:
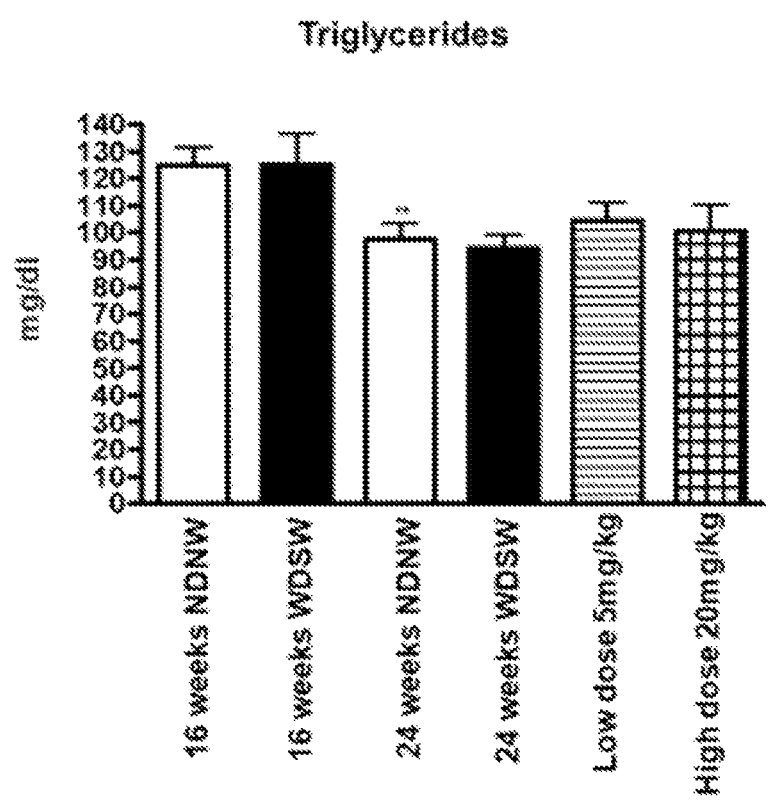
FIG. 7 is a diagram showing a histogram analysis of serum triglycerides in mice 16 weeks NDNW vs 24 weeks NDNW (P value P: 0.003).

Shown in FIG. 7 is triglyceride data. There was no significant difference in serum triglycerides between the WDSW and fluasterone-treated mice.

Figure 8:
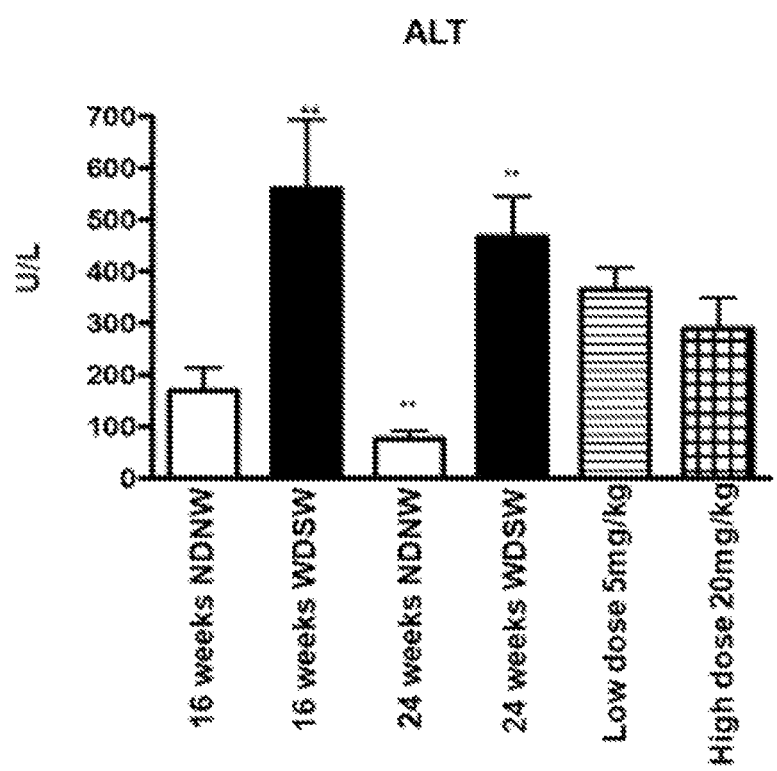
FIG. 8 is a diagram showing a histogram analysis of ALT in mice 16 weeks NDNW vs 16 weeks WDSW (P value P: 0.007); 16 weeks NDNW vs 24 weeks NDNW (P value P: 0.02); and 24 weeks NDNW vs 24 weeks WDSW (P value P<0.001).

Shown in FIG. 8 is ALT data. In mice, ALT was the best measure of liver function; elevations indicate liver damage. There was a strong trend towards improved ALT (lower ALT) in the treated mice vs. the 24 week positive control. The P values for 24 wk WDSW vs. Low Dose and High Dose treatment groups were 0.11 and 0.051, respectively. The fluasterone treatment significantly improved the condition of the livers.

Figure 9:
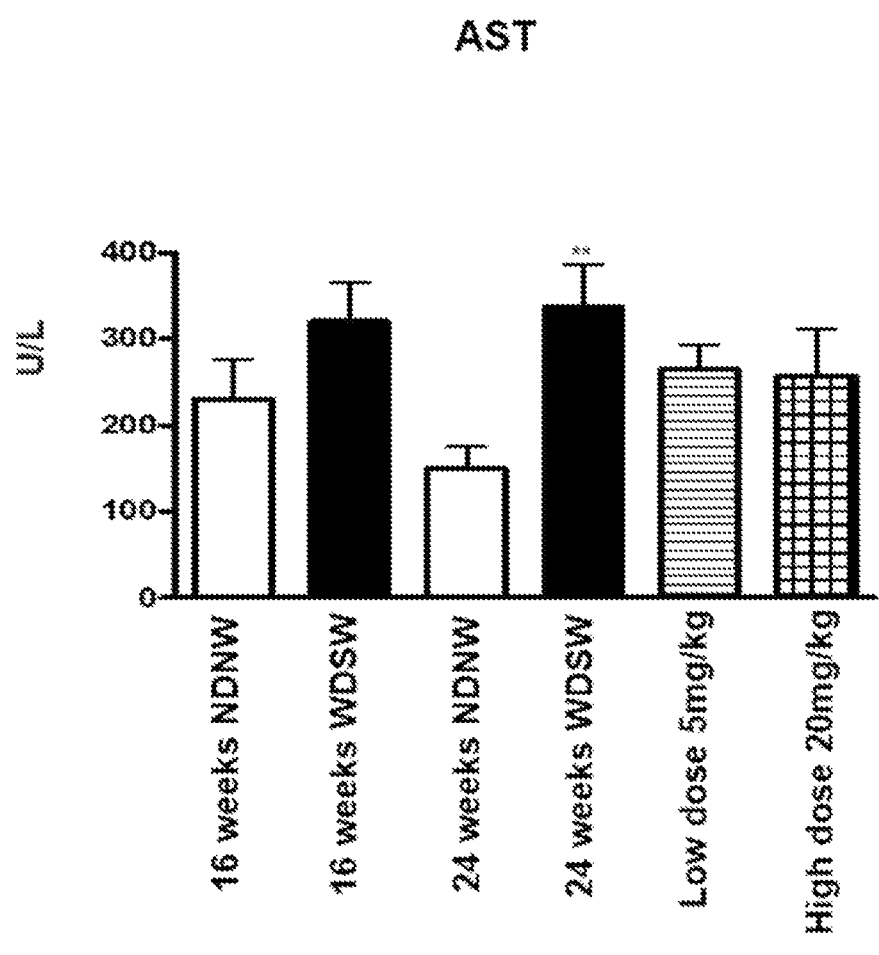
FIG. 9 is a diagram showing a histogram analysis of AST in mice 24 weeks NDNW vs 24 weeks WDSW (P value P<0.002); and 24 weeks WDSW vs 24 WDSW weeks low dose (P value 0.1).

Shown in FIG. 9 is AST data. There was a statistically significant drop in AST in the low dose fluasterone-treated mice relative to the 24 week WDSW; the low dose group had lower AST than the WDSW control, albeit only at P=0.10.

Figure 10:
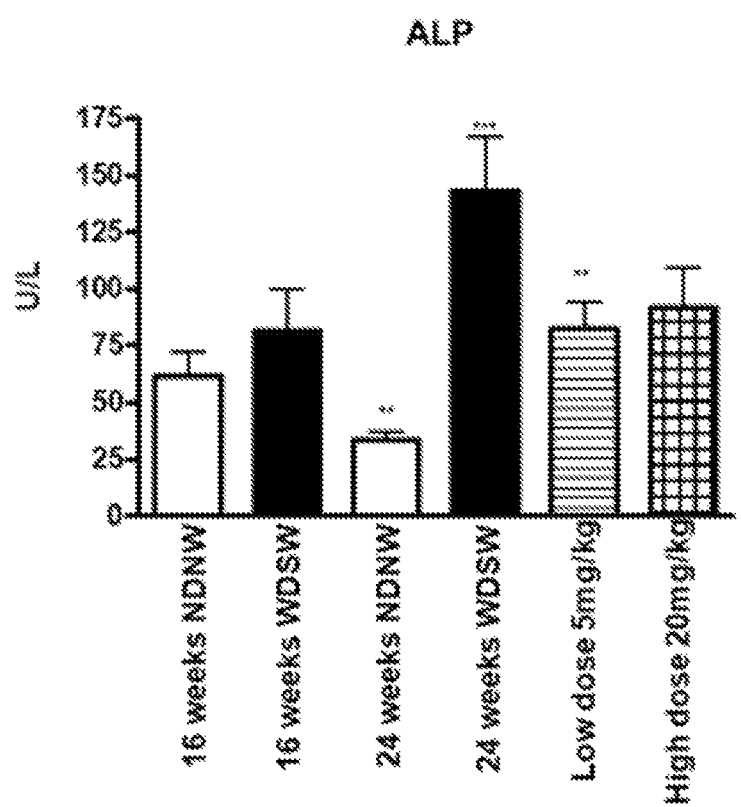
FIG. 10 is a diagram showing a histogram analysis of alkaline phosphatase (ALP) in mice 16 weeks NDNW vs 24 weeks NDSW (P value P: 0.005); and 24 weeks NDSW vs 24 weeks WDSW (P value P<0.0001). 24 weeks WDSW vs 24 weeks low dose 5 mg/Kg (P value P: 0.01).

Shown in FIG. 10 is alkaline phosphatase (ALP) data. ALP was significantly lower in the low dose fluasterone-treated group vs. the WDSW control (P=0.01), and the high dose fluasterone-treated group showed a strong trend to improvement (P=0.058). High ALP indicates that the liver has been damaged or that there is bone lysis; some other anti-diabetic drugs (such as saroglitazar) can cause increases in ALP while improving insulin sensitivity.

Pathology analysis of the liver was also carried out. Liver samples in formalin were allowed to fix for 36-48 hours depending on the size of the sample and processed into FFPE blocks immediately after fixation. Slides were stained with H&E for visualizing hepatic steatosis (fat content), inflammation, and hepatocyte ballooning; and Sirius Red for visualizing fibrosis. H&E stained slides cut from FFPE blocks were prepared, read and scored. Steatosis percentage (%), Steatosis (Grade 0-3), Ballooning (0-2), Lobular inflammation (0-3), NAS, SAF Activity (Ballooning+inflammation), Fibrosis (NASH CRN), Perisinusoidal fibrosis (0,1,2), and NASH Category (0=normal, 1=steatosis, 2=NASH) were graded. As mentioned above, slides were also stained with Sirius Red for collagen morphology. The following histology images (not shown) of H&E and Sirius Red stained samples (5 slides each) were used for the analysis: 16 Week Western Diet Sugar Water (Positive Control) H&E 5×; 16 Week Western Diet Sugar Water (Positive Control) Sirius Red 5×; 16 Week Normal Diet Normal Water (negative Control) H&E 5×; 16 Week Normal Diet Normal Water (negative Control) Sirius Red 5×; 24 Week Western Diet Sugar Water (Positive Control) H&E 5×; 24 Week Western Diet Sugar Water (Positive Control) Sirius Red 5×; 24 Week Normal Diet Normal water (Negative Control) H&E 5×; 24 Week Normal Diet Normal water (Negative Control) SIRIUS RED 5×; 24 Week Western Diet Sugar Water (High Dose) H&E 5×; 24 Week Western Diet Sugar Water (High Dose) Sirius Red 5×; 24 Week Western Diet Sugar Water (Low Dose) H&E 5×; 24 Week Western Diet Sugar Water (Low Dose) Sirius Red 5×.

Figure 11:
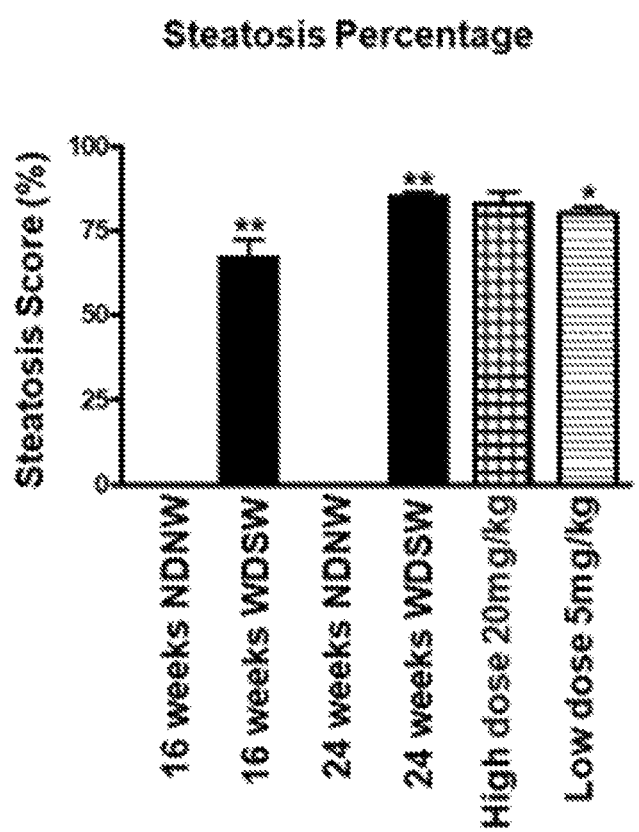
FIG. 11 is a diagram showing a histogram analysis of steatosis percentage, 16 weeks NDNW vs 16 weeks WDSW (P value P<0.001); 16 weeks NDNW vs 24 weeks NDNW (P value P<0.001); 24 weeks NDNW vs 24 weeks WDSW (P value P<0.001); and 24 weeks WDSW vs 24 weeks low dose (P value P<0.032).
Figure 12:
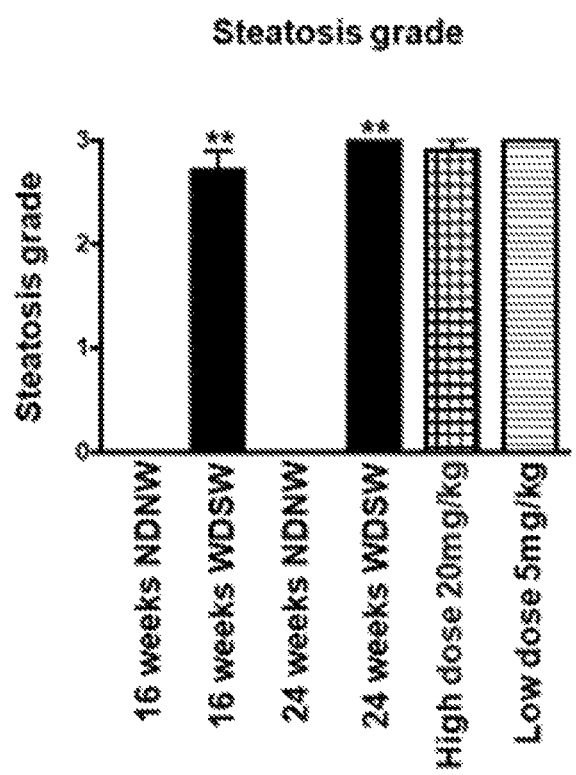
FIG. 12 is a diagram showing a histogram analysis of steatosis grade, 16 weeks NDNW vs 16 weeks WDSW (P value P<0.001). 24 weeks NDNW vs 24 weeks WDSW (P value P<0.001).

Shown in FIGS. 11 and 12 are steatosis percentage and steatosis grade data, respectively. The low dose treatment group had statistically significantly less steatosis percentage compared to positive controls (P=0.032), but neither treatment group had improved steatosis grade when compared with the positive controls.

Figure 13:
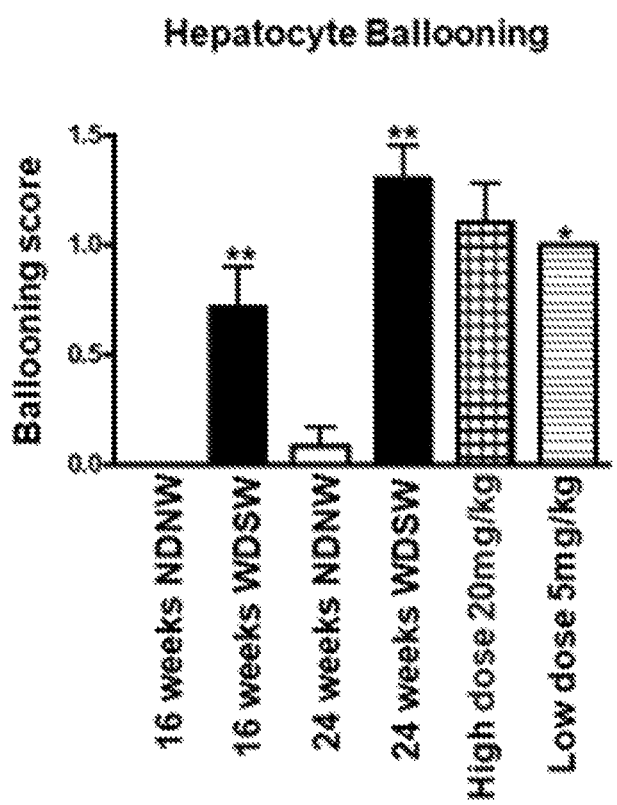
FIG. 13 is a diagram showing a histogram analysis of hepatocyte ballooning, 16 weeks NDNW vs 16 weeks WDSW (P value P<0.001); 24 weeks NDNW vs 24 weeks WDSW (P value P<0.001); and 24 weeks WDSW vs 24 weeks low dose (P value P<0.02).

Shown in FIG. 13 is hepatocyte ballooning data. The low dose treatment group had statistically less ballooning than the 24 week positive control (P=0.026).

Figure 14:
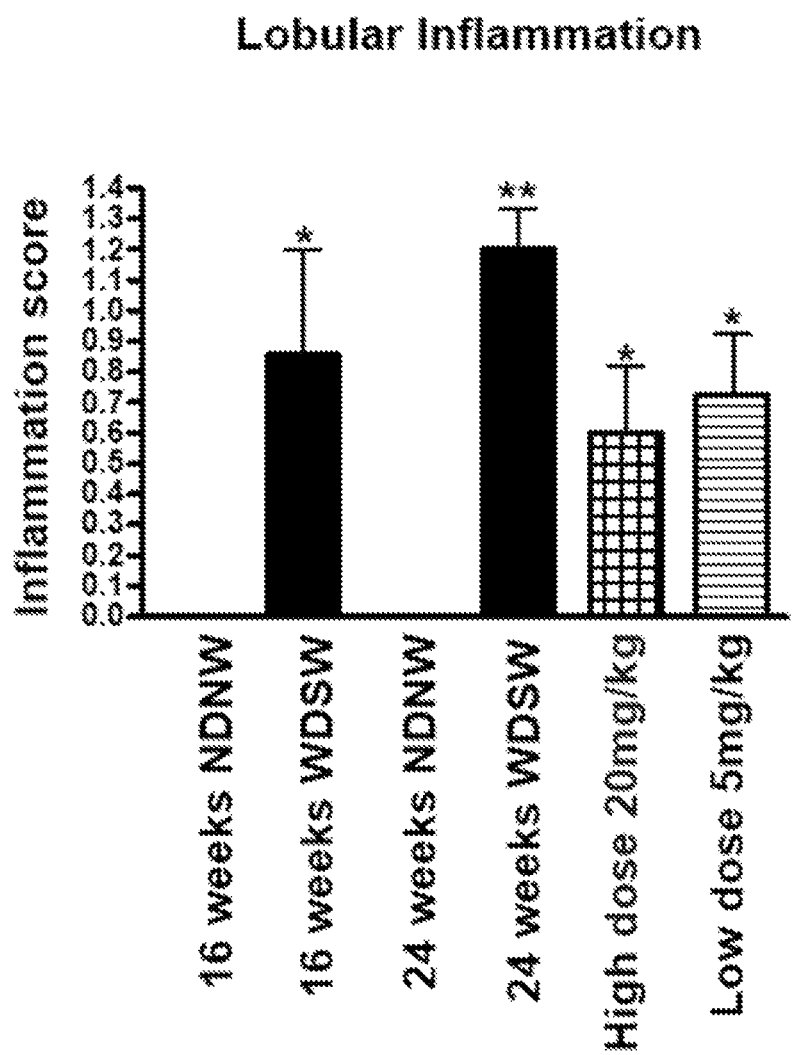
FIG. 14 is a diagram showing a histogram analysis of lobular inflammation, 16 weeks NDNW vs 16 weeks WDSW (P value P<0.05); 24 weeks NDNW vs 24 weeks WDSW (P value P<0.001); 24 weeks WDSW vs 24 weeks High dose (P value P<0.01); and 24 weeks WDSW vs 24 weeks low dose (P value P<0.032).

Shown in FIG. 14 is lobular inflammation data. Fluasterone significantly reduced inflammation in both treatment groups.

Figure 15:
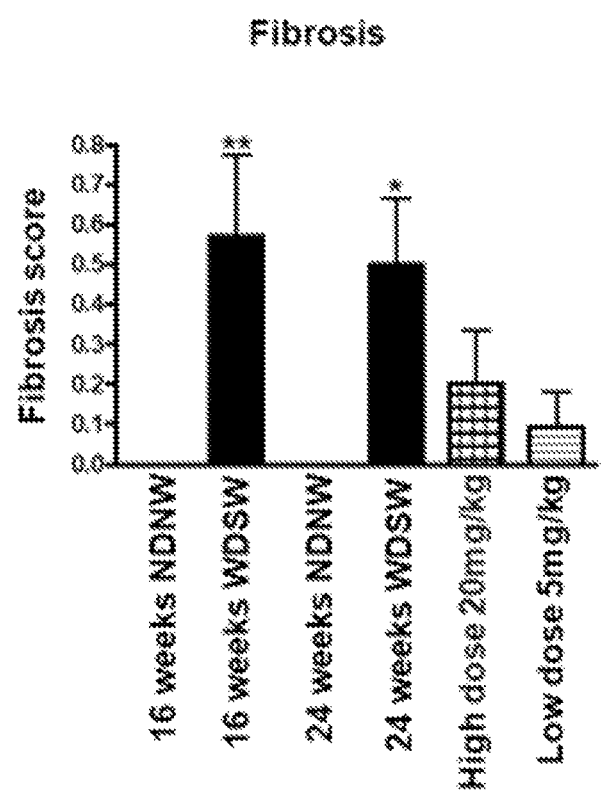
FIG. 15 is a diagram showing a histogram analysis of fibrosis, 16 weeks NDNW vs 16 weeks WDSW (P value P<0.005); and 24 weeks NDNW vs 24 weeks WDSW (P value P<0.05).

Shown in FIG. 15 is fibrosis data. Inflammation and ballooning occur before fibrosis, and the development of fibrosis requires and is driven by increasing inflammatory signaling in the liver. 5/10 of the 24 week WDSW group progressed to fibrosis measured by NASH CRN score, whereas only 2/10 from the high dose and 1/10 from the low dose progressed to measurable fibrosis by NASH CRN score. Thus, fewer fluasterone-treated mice developed measurable fibrosis. There was a strong trend to improvement in fibrosis in the fluasterone-treated groups, with the low dose group lower than the 24 week positive controls (P=0.057) almost reaching statistical significance. The high dose group was not statistically less fibrotic although there was a trend (P=0.15).

Figure 16:
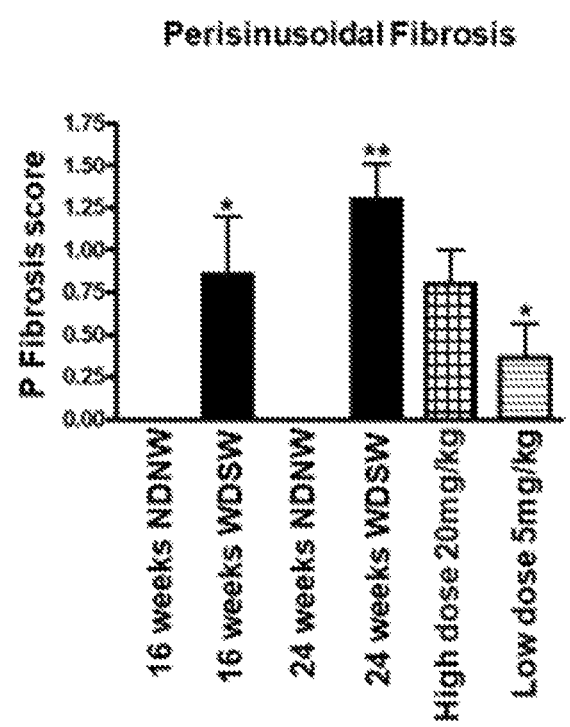
FIG. 16 is a diagram showing a histogram analysis of perisinusoidal fibrosis, 16 weeks NDNW vs 16 weeks WDSW (P value P<0.05); 24 weeks NDNW vs 24 weeks WDSW (P value P<0.001); and 24 weeks WDSW vs 24 weeks low dose (P value P<0.01).

Shown in FIG. 16 is perisinusoidal fibrosis data. The low dose fluasterone-treated group had significantly less perisinusoidal fibrosis (P=0.002). The high dose group was almost statistically significant, with a P value of 0.052.

Figure 17:
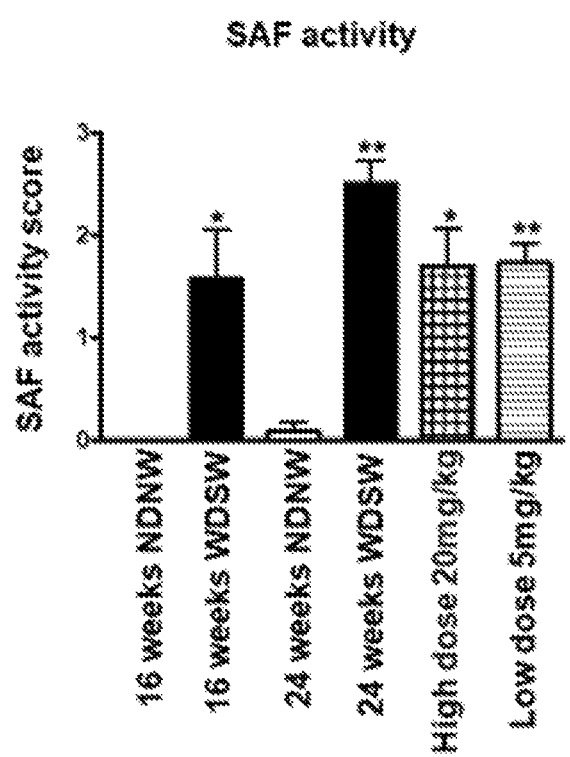
FIG. 17 is a diagram showing a histogram analysis of SAF activity score, 16 weeks NDNW vs 16 weeks WDSW (P value P<0.01); 24 weeks NDNW vs 24 weeks WDSW (P value P<0.001). 24 weeks WDSW vs 24 weeks High dose (P value P<0.039). 24 weeks WDSW vs 24 weeks low dose (P value P<0.008).

Shown in FIG. 17 is SAF Activity score. The SAF Activity score is the addition of ballooning (from 0 to 2) and lobular inflammation (from 0 to 2). Compared to the NAS, the SAF activity score does not include steatosis and is more closely associated with risk of disease progression. Fluasterone improved the SAF scores in both treatment groups compared to the 24 week positive controls.

Figure 18:
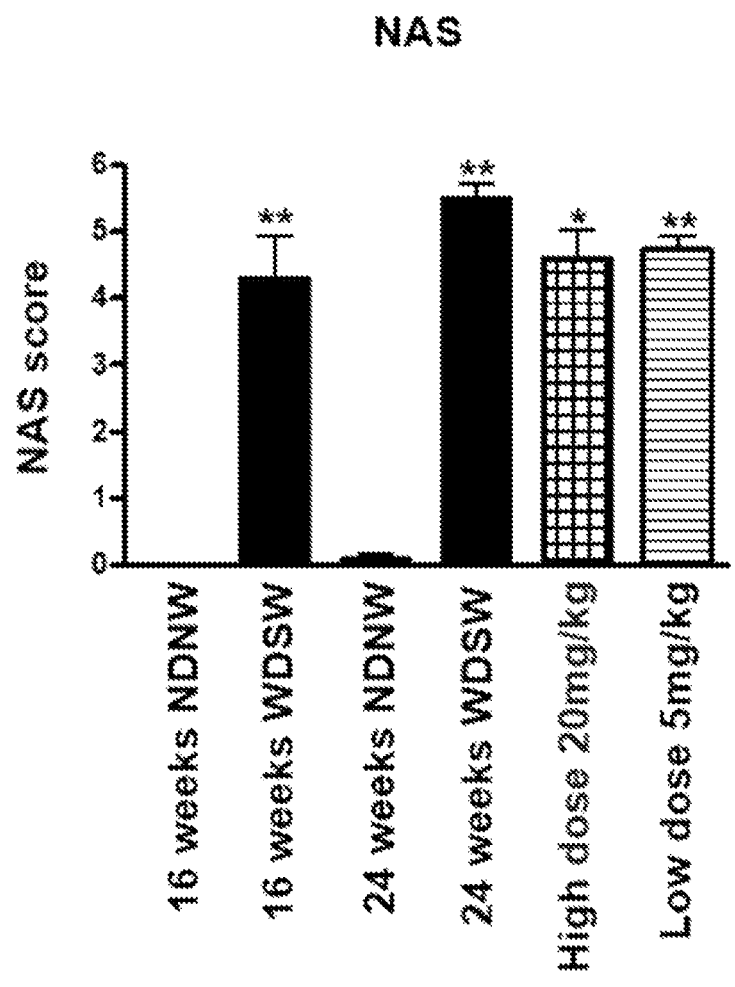
FIG. 18 is a diagram showing a histogram analysis of NAS Score, 16 weeks NDNW vs 16 weeks WDSW (P value P<0.001); 24 weeks NDNW vs 24 weeks WDSW (P value P<0.001); 24 weeks WDSW vs 24 weeks High dose (P value P<0.05); and 24 weeks WDSW vs 24 weeks low dose (P value P<0.001).

Shown in FIG. 18 is NAS score. The NAS score is the sum score of steatosis, lobular inflammation, and ballooning. Fluasterone improved the NAS score in both fluasterone-treatment groups compared to the 24 week positive controls.

Thus, it is clear from the above-described data that fluasterone treated groups (low and high dosage) show significant improvements in physiological parameters such as fasting blood glucose, serum LFTs (Liver Function Tests) and lipids, as well as liver pathology scores compared to positive natural history controls.

Progression to NASH: At baseline (16 weeks), 5/10 mice were categorized as having full NASH. In the 24 week WDSW positive natural history control group, 10/10 mice developed NASH. In the low dose fluasterone-treated group, 7/10 developed NASH, and in the high dose group only 5/10 progressed to NASH. In other words, the fluasterone treatment halted the progression of NASH.

The disclosures of each and every patent, patent application, GenBank record, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed is:

1. A method for the treatment of an individual suffering from non-alcoholic steatohepatitis comprising administering to the individual in need of such treatment an effective amount of a compound according to Formula I:

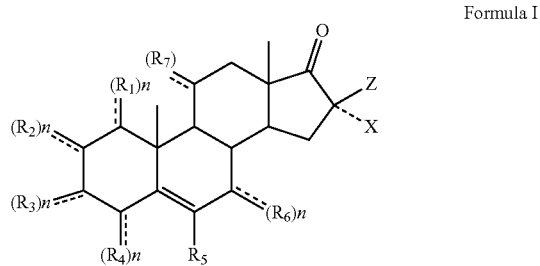

Formula I wherein:
$R_1$, $R_2$, $R_4$, $R_5$, $R_6$, and $R_7$ are each individually hydrogen, hydroxyl, —($C_1$-$C_6$)alkyl or —($C_1$-$C_6$)alkoxy;
each $R_3$ is individually halogen, hydrogen, hydroxyl, —($C_1$-$C_6$)alkyl or —($C_1$-$C_6$)alkoxy;
X is halogen, hydroxyl, hydrogen, —($C_1$-$C_6$)alkyl or —($C_1$-$C_6$)alkoxy;
Z is hydrogen, —($C_1$-$C_6$)alkyl or —($C_1$-$C_6$)alkoxy, and n is 1 or 2,
wherein stereochemistry of various substituents is designated as being in the α-position (alpha-position), or below the plane of the paper, by means of a broken line (---) joining said substituents to the steroid nucleus, and wherein the compound of Formula I is 16α-fluoro-5-androsten-17-one.

2. The method according to claim 1 wherein the compound of Formula I is administered in a pharmaceutical composition comprising nanosized particles of the Formula I compound suspended in a mixture comprising a ($C_1$-$C_6$) alkyl alcohol, a surfactant, and optionally, a long chain alcohol.

3. The method according to claim 2 wherein the surfactant is a polysorbate or a polyethyleneglycol substituted fatty acid.

4. The method according to claim 3 wherein the polysorbate is selected from the group consisting of polyoxyethylene-20-sorbitan monooleate (Tween 80), polyoxyethylene-20-sorbitan monostearate (Tween 60), polyoxyethylene-20-sorbitan monopalmitate (Tween 40), polyoxyethylene-20-sorbitan monolaurate (Tween 20), polyethyleneglycol stearate, polyethyleneglycol oleate, and mixtures thereof.

5. The method according to claim 4 wherein the polysorbate is polyoxyethylene-20-sorbitan monooleate (Tween 80), and wherein said pharmaceutical composition comprises a ($C_1$-$C_6$)alkyl alcohol in the range of from about 30 to about 90% (v/v), polyoxyethylene-20-sorbitan monooleate (Tween 80) in the range of from about 0.01% to about 3.5% and water in the range of from about 0% to about 60%.

6. The method according to claim 2, wherein the pharmaceutical composition comprising nanosized particles is in the form of a gel, and further comprises water and a thickening agent, and optionally a base.

7. The method according to claim 1, wherein the compound of Formula I is administered transdermally.

8. The method according to claim 7, wherein the compound of Formula I is administered at a dose of from about 12 to about 150 mg/day.

9. A method for the treatment of an individual suffering from non-alcoholic steatohepatitis comprising administering to the individual in need of such treatment a pharmaceutical composition comprising an effective amount of a compound according to Formula I:

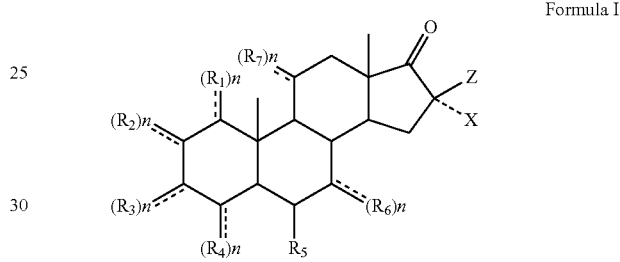

Formula I wherein:
$R_1$, $R_2$, $R_4$, $R_5$, $R_6$, and $R_7$ are each individually hydrogen, hydroxyl, —($C_1$-$C_6$)alkyl or —($C_1$-$C_6$)alkoxy;
each $R_3$ is individually halogen, hydrogen, hydroxyl, —($C_1$-$C_6$)alkyl or —($C_1$-$C_6$)alkoxy;
X is halogen, hydroxyl, hydrogen, —($C_1$-$C_6$)alkyl or —($C_1$-$C_6$)alkoxy;
Z is hydrogen, —($C_1$-$C_6$)alkyl or —($C_1$-$C_6$)alkoxy, and n is 1 or 2,
wherein stereochemistry of various substituents is designated as being in the α-position (alpha-position), or below the plane of the paper, by means of a broken line (---) joining said substituents to the steroid nucleus, and wherein the compound of Formula I is 16α-fluoro-5-androsten-17-one.

10. The method according to claim 9, wherein the composition comprises a surfactant.

11. The method according to claim 10, wherein the surfactant is polyoxyethylene-20-sorbitan monooleate (Tween 80).

12. The method according to claim 10, wherein the pharmaceutical composition is administered at a dose of from about 5 mg to about 150 mg per day.

13. The method according to claim 12, wherein the pharmaceutical composition is administered subcutaneously.

14. The method according to claim 12, wherein the pharmaceutical composition is administered transdermally.

* * * * *